(12) United States Patent
Lee et al.

(10) Patent No.: US 7,029,921 B2
(45) Date of Patent: *Apr. 18, 2006

(54) APPARATUS FOR RAPID MEASUREMENT OF AEROSOL BULK CHEMICAL COMPOSITION

(75) Inventors: Yin-Nan E. Lee, East Setauket, NY (US); Rodney J. Weber, Atlanta, GA (US); Douglas Orsini, Aubiere Cedex (FR)

(73) Assignee: Brookhaven Science Associates, LLC, Upton, NY (US)

( * ) Notice: Subject to any disclaimer, the term of this patent is extended or adjusted under 35 U.S.C. 154(b) by 538 days.

This patent is subject to a terminal disclaimer.

(21) Appl. No.: 10/279,510

(22) Filed: Oct. 24, 2002

(65) Prior Publication Data
US 2003/0082825 A1  May 1, 2003

Related U.S. Application Data

(63) Continuation-in-part of application No. 09/679,704, filed on Oct. 5, 2000, now Pat. No. 6,506,345.

(51) Int. Cl.
*G01N 31/00* (2006.01)

(52) U.S. Cl. ............... 436/148; 436/146; 436/174; 436/179; 436/181; 422/100; 422/83; 422/73; 422/81; 422/68.1; 73/28.01; 73/28.04; 73/28.05; 73/61.06

(58) Field of Classification Search ............ 436/146, 436/148, 174, 179, 181; 422/100, 83, 73, 422/81, 68.1; 73/28.01, 28.04, 28.05, 61.06
See application file for complete search history.

(56) References Cited

U.S. PATENT DOCUMENTS

| 4,868,398 A | 9/1989 | Mulcey et al. |
| 5,855,652 A | 1/1999 | Talley |
| 6,506,345 B1 * | 1/2003 | Lee et al. .............. 422/100 |

OTHER PUBLICATIONS

Boring, C.B, R. Al-Horr, Z. Genfa, andP.K. Dasgupta, "Field measurement and soluble anions in atmospheric particulate matter using a parallel plate wet denuder and an alternating filter-based automated analysis system," *Anal. Chem*, 74: 1258 (2002).

(Continued)

*Primary Examiner*—Jill Warden
*Assistant Examiner*—Sam P. Siefke
(74) *Attorney, Agent, or Firm*—Margaret C. Bogosian

(57) ABSTRACT

An apparatus for continuous on-line measurement of chemical composition of aerosol particles with a fast time resolution is provided. The apparatus includes an enhanced particle size magnifier for producing activated aerosol particles and an enhanced collection device which collects the activated aerosol particles into a liquid stream for quantitative analysis by analytical means. Methods for on-line measurement of chemical composition of aerosol particles are also provided, the method including exposing aerosol carrying sample air to hot saturated steam thereby forming activated aerosol particles; collecting the activated aerosol particles by a collection device for delivery as a jet stream onto an impaction surface; and flushing off the activated aerosol particles from the impaction surface into a liquid stream for delivery of the collected liquid stream to an analytical instrument for quantitative measurement.

13 Claims, 13 Drawing Sheets

OTHER PUBLICATIONS

Buhr, S.M, M.P. Buhr, F.C. Fehsenfeld, J.S. Holloway, U. Karst, R.B. Norton, D.D. Parrish and R.E. Slever, "Development of a semi-continous method for the measurement of nitric acid vapor and particulate nitrate and sulfate," *Atmos. Environ.* 29: 2609-2624 (1995).

Carson, P.G., K.R. Neubauer, M.V. Johnston, and A.S. Wexler, "On-line chemical analysis of aerosols by rapid single-particle mass spectrometry," *J. Aerosol Sci.* 26: 535-545, (1995).

Chow, J.C., "Measurement method to determine compliance with ambient air quality standards for suspended particles," *J. Air West Mang.* 45: 320-382, (1995).

Hinz, K.P., R. Kaufmann, and B. Spengler, "Laser-Induced mass analysis of single particles in the airborne state," *Analyt. Chem.* 66: 2017-2076, (1994).

Ito, I., C.C. Chasteen, H. Chung, S.K. Prouthoor, Z. Genfa,, and P.K. Dasgupta, "A continuous monitoring system for strong acidity in aerosols," *Anal. Chem*, 70: 2839-2847, (1998).

Jayne, J.T., D.C. Leard, X. Zhang, P. Davidovits, K.A. Smith, C.E. Kolb, and D.R. Worsnop, "Aerosol mass spectrometer for size and composition analysis of submicron particles," *J. Aerosol Sci*, 33:49-70, (2002).

Karlsson, A., K. Irgum, and H. Hansson, "Single-state flowing liquid film impactor for continuous on-line particle analysis," *J. Aerosol Sci.* 28: 1539-1551, (1997).

Khlyatov, A., G.P. Wyers, and J. Slamina, "The steam-jet aerosol collector," *Atmos. Envir.* 29: 2229-2234 (1995).

Knutson, E.O., and K.T. Whitby, "Aerosol classification by electrical mobility Apparatus, theory, and applications," *J. Aerosol Sci.* 6: 443-451, (1975).

Kogan, Y.I., and Z.A. Burnasheva, "Growth and measurement of condensation nuclei in a continuous stream," *Russian J. Phys. Chem.* 34: 1240-1243, (1960).

Kousaka, Y., T. Nikla, K. Okuyama, and H. Tanaka, "Development of a mixing type condensation nucleus counter," *J. Serosol Sci.* 13: 231-340, (1982).

Liu, S. and P.K. Dasgupta, "Automated system for chemical analysis of airborne particles based on corona-free electrostatic collection," *Anal. Cehm*, 68: 3638-3644, (1996).

Marljinissen, J.C.M., B. Scarlett, and P.J.T. Verheljen, "Proposed on-line aerosol analysis combining size determination, laser-induced fragmentation and time-of-flight mass spectroscopy," *J. Aerosol Sci*, 19: 1307, (1988).

Marple, V.A., and K. Willeke, "Impactor design," *Atmos. Envir.* 10: 891-898, (1976).

McKeown, P.J., M.V. Johnston, and D.D. Murphy, "On-line single-particle aerosol analysis by laser description mass spectrometry," *Analys. Chem.* 63: 2069, (1991).

Okuyame, K., Y. Kousaka and T. Motouchi, "Condensational growth of ultrafine aerosol particles in a new particle size magnifier," *Aerosol Sci. and Technol*. 3: 353-366 (1984).

Oms, T.T., P.A.C, Jongejan, A.C. Veltkamp, G.P. Wyers, and J. Slamina, "Continuous monitoring of atmospheric HC1, $HNO_2$, and $SO_2$ by wet-annular denuder sampling with on-line chromatographic analysis," *Intern. J. Anal. Chem.* 2: 207-218, (1997).

Poruthoor, S.K., and P.K. Dasgupts, "Automated particle collection and analysis. Near-real time measurement of aerosol cerium (III)," *Analytica Chemica Acta* 361: 151-159, (1998).

Prather, K.A., T. Nordmeyer, and K. Salt, "Real-time characterization of individual aerosol particles using time-of-flight mass spectrometry," *Analyt. Chem.* 66: 1403, (1994).

Rader, D.J., and V,A. Marple, "Effects of ultre-stokesian drag and particle interception on Impaction characteristics." *Aerosol Sci. Technol*, 4: 141-156, (1985).

Reents, W.D.J., A.M. Mujece, A.J. Muller, D.J. Siconolfi, and A.G. Swanson, "Real-time elemental analysis of individual submicron particles by laser ablation time-of flight mass spectrometry," *J. Aerosol Sci*. 23: 263, (1995).

Seebaugh, W.R. and B.G. LaFleur, "Low turbulence inlet for aerosol sampling from aircraft," *AAAR*, Orlando, Oct. 14-18.

Simon, P.K., and P.K. Dasgupta, "Continuous automated measurement of the soluble fraction of atmospheric particulate matter," *Anal Chem*. 67: 71-78, (1995).

Slanina, J,, H.M.T. Brink, R.P. Otjes, A. Even, P. Jonejan, A. Khiystov, A, Waijers-Ijpelaan, M. Hu and Y. Lu, "The continuous analysis of nitrate and ammonium in aerosols by the steam jet aerosol collector (SJAC): Extension and validation of the methodology," *Envir*, 35: 2319-2330, (2001).

Slanina, J., H.M.T. Brink, R.P. Otjes, A. Evan, P. Jonejan. A. Khlystov, A. Waijers-Ijpelaan, M. Hu and Y. Lu, "The continuous analysis of nitrate and ammonium in aerosols by the steam jet aerosol collector (SJAC): Extension and validation of the methodology," *Envir*, 35: 2319-2330, (2001).

Stolzenburg, M.R. and V. Hering, "A method for the automated measurement of fine particle nitrate in the atmosphere," *Environ, Sci. Technol*, 34: 904-914 (2000).

Turpin, B.J., R.A. Cary, and J.J. Huntzicker, "An in situ, time-resolved analyzer for aerosol organic and elemental carbon," *J. Aerosol Sci*. 12: 161-171, (1990).

Toon, J., "Measuring Atmospheric Pollutants: Instrument Automates Sampling of Aerosols and Provides More Detailed Data;" complete set attached. gtresearchnews.gatech.edu Newsrelease/PILS.htm, Aug. 28, 2002.

Wang, S.C., and R.C. Flagan, "Scanning electrical mobility spectrometer," *Aerosol Sci. Technol*. 13: 230-240, (1990).

Weber, R.J., D. Orsini, Y. Daun, Y.N. Lee, P. Klotz, and F. Brechtel, "A particle- into-liquid collector for rapid measurements of aerosol chemical composition," *Aerosol Sci. Tech*, 35: 718-727.

Zellweger, C., M. Ammann, P. Hofer, and U. Baltensperger, "NOy specification with combined wet effluent diffusion denuder-aerosol collector coupled to ion chromatography," *Atm. Envir*, 33: 1131-1140, (1999).

* cited by examiner

Schematic diagram for mass collection efficiency calibration of the PILS coupled to a dual channel ion chromatograph.

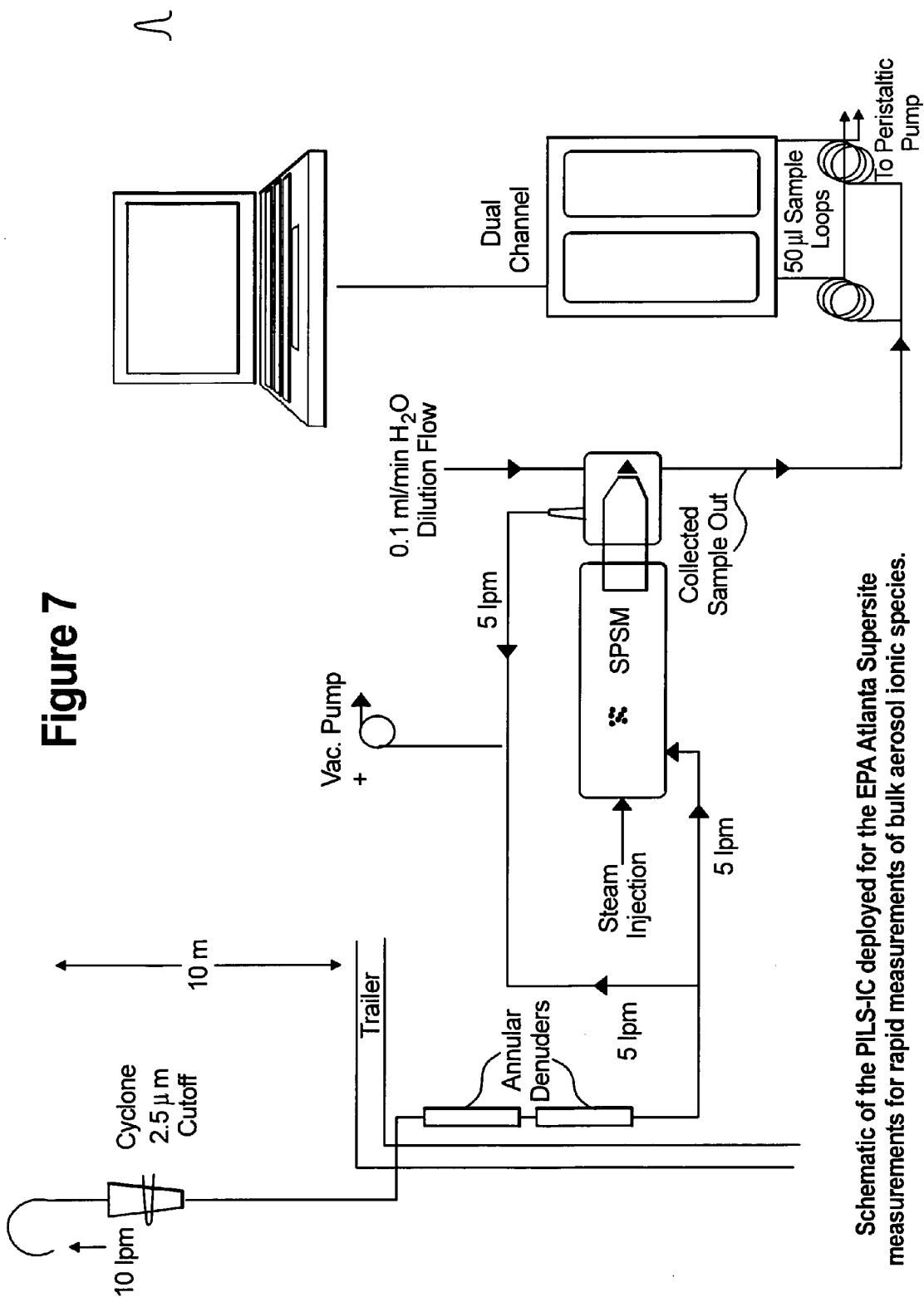

PILS-IC Measurements of sulfate concentrations and ammonium to sulfate molar ratios recorded at the Atlanta Supersite.

APPARATUS FOR RAPID MEASUREMENT OF AEROSOL BULK CHEMICAL COMPOSITION

RELATED APPLICATION

This application is a continuation-in-part of U.S. application Ser. No. 09/679,704 filed on Oct. 5, 2000 now U.S. Pat. No. 6,506,345, entitled "An Apparatus for Rapid Measurement of Aerosol Bulk Chemical Composition," which is incorporated herein by reference.

This invention was made with Government support under contract number DE-AC02-98CH10886, awarded by the U.S. Department of Energy. The Government has certain rights in the invention.

BACKGROUND OF THE INVENTION

1. Field of Invention

The invention relates to an apparatus for rapid automated on-line continuous measurement of chemical composition of ambient aerosol particles. This invention also relates to a method of analyzing the chemical composition of ambient aerosol particles.

2. Description of Related Art

There have been many devices built and many processes developed to understand the sources, atmospheric transformation, fate and health effects of ambient aerosols. All require knowledge of particle chemical composition. Most processes using these devices are quantitative composition measurements, typically performed off-line on particles collected onto substrates by filtration or inertial impaction. Samples collected on the substrates are then manually extracted and analyzed. For example, measurements of ionic aerosol components involve collection on denuder-filter pack assemblies, extraction of the collected aerosol into water, and analysis of the extract for various ionic species using an ion chromatography (IC) technique. Unfortunately, although widely used, this approach has many drawbacks. Additionally, depending on flow rates and ambient concentrations, the sampling intervals are long, typically hours to days. Faster measurements are possible but often impractical due to the labor involved in filter preparation and sample extraction. This is particularly true in long-term air quality monitoring programs. Since the turn-around time for processed results also tends to be long, immediate insight and interpretation of these results are generally not available for in-the-field adjustment and modifications of experiment sampling strategies and protocols.

In addition, off-line techniques are also prone to potential sampling artifacts, particularly for volatile aerosol components. Artifacts that lead to measurement errors are due to particle/gas, particle/particle, gas/substrate, and particle/substrate interactions (Chow, 1995). These interactions occur because particles are removed from the gas, concentrated on the substrate, and then exposed to different conditions for extended periods during sampling and storage. During sampling, volatile chemical components can be adsorbed or lost as result of changes in temperature, relative humidity, and ambient particle and gas composition. Pressure drops within the sampler can also contribute to volatility losses. These artifacts have led to complicated filter pack sampling systems using multiple filters of various types to capture volatile aerosol components. Artifacts may also be introduced in the preparation and extraction of filters. Combined, these processes can lead to significant uncertainties, particularly when measuring mass concentrations of volatile or easily contaminated aerosol chemical components, such as nitrate, ammonium, and semi-volatile organic species.

Advanced instruments for real-time size-resolved measurements of particle chemical composition involving mass spectrometers have been developed (Carson et al., 1995; Hinz et al., 1994; Jayne et al., 1998; Marijinissen et al., 1988; McKeown et al., 1991; Prather et al., 1994; Reents et al., 1995). These techniques provide important insights into particle composition at single particle resolution. Unfortunately, they tend to be complex and costly, and the measurements generally do not give quantitative information on particle composition.

Other approaches involving automated bulk composition measurements have been developed. These approaches provide faster measurements and minimize some of the sampling artifacts associated with the off-line techniques. Although they do not provide size-resolved information as do mass spectrometer-based instruments, these approaches are quantitative. One common approach is to convert the aerosol particles to a vapor and measure selected evolved gases. For example, Turpin et al. (1990) developed a technique for carbonaceous aerosols by measuring the quantity of carbon dioxide produced when a loaded filter is heated to various temperatures. Stolzenburg and Hering (1999) developed an instrument that collects particles by impaction and measures various evolved gases when the deposited aerosol is flash vaporized. This approach has been successfully used to measure nitrate, and also shows promise for sulfate and carbonaceous aerosol components.

Other devices have been developed that bypass the filter or impactor sampling used in the off-line approaches for measurement of aerosol ionic species. In this case, the same analytical technique is employed, except the particles are collected directly into a liquid for automatic analysis by ion chromatography. Techniques for capturing the particles vary. Automated systems have been developed that collect particles onto a filter that is periodically washed (Buhr et al., 1995), or particles are directly impacted into a flowing liquid (Karlsson et al., 1997). In another approach, ambient particles are first grown to large water droplets by mixing with air saturated with water vapor. The large droplets are then captured onto surfaces by various inertial techniques, and combined with condensed water vapor, produce the liquid stream for analysis. A variety of instruments have been developed using this approach (Ito et al., 1998; Khlystov et al., 1995; Liu and Dasgupta, 1996; Oms et al., 1997; Poruthoor and Dasgupta, 1998; Simon and Dasgupta, 1995; Zellweger et al., 1999). Drawbacks associated with these techniques include aerosol losses, greater complexity due to the need for sample pre-concentration, and slow time response due to the time needed to drain large wetted areas.

What is needed, therefore, is an instrument designed specifically for rapid measurement of the chemical components of ambient aerosols.

OBJECTS OF THE INVENTION

It is an object of the invention to provide an apparatus and process for automated on-line continuous measurement of ambient aerosol bulk chemical composition.

It is another object of the invention to provide an apparatus and process for rapid and quantitative on-line measurement of ambient aerosol bulk chemical composition.

It is another object of the invention to provide an apparatus and process for measurement of ambient aerosol bulk composition which is not complex and is cost effective.

SUMMARY OF THE INVENTION

The present invention, which addresses the needs of the prior art and meets the objects of the invention, provides apparatuses and methods for continuous on-line measurement of chemical composition of aerosol particles. More specifically, one apparatus is provided that includes a modified particle size magnifier containing a mixing chamber and a growth chamber in fluid communication with each other and a collection device disposed downstream and in fluid communication with the growth chamber of the particle size magnifier. The collection device is preferably an inertial impactor which has a single circular nozzle and is enclosed in a housing having an impaction surface opposite the circular nozzle. The collection device also has an inlet for drawing sample air, another inlet adapted to receive carrier water and a drain, all in fluid communication with the impactor housing.

Sample air carrying fine aerosol particles enters the mixing chamber of the particle size magnifier where hot saturated steam condenses upon the fine aerosol particles producing activated aerosol particles droplets in the growth chamber of the particle size magnifier which are then collected by inertial techniques.

A single jet inertial impactor can be used to collect the activated aerosol particles onto a vertical glass plate that is continually washed with a constant water carrier flow of 0.10 mL min$^{-1}$. The flow from the inertial impactor is divided and analyzed by a dual channel ion chromatograph (IC). In its current form, 4.3-minute integrated samples were measured every 7 minutes. The apparatus of the invention provides bulk composition measurements with a detection limit of approximately 0.1 μg m$^{-3}$ for ionic species such as chloride, nitrate, sulfate, sodium, ammonium, calcium, potassium, oxalate, acetate, and formate and methane sulfonate.

In another aspect, an enhanced apparatus for continuous on-line measurement of chemical composition of aerosol particles is provided, the enhanced apparatus including an enhanced particle size magnifier having a mixing and a growth chamber in fluid communication with each other and a collection device disposed downstream and in fluid communication with the growth chamber.

The mixing chamber has a first inlet, a second inlet and an outlet, the first inlet adapted to receive sample air carrying aerosol particles, the second inlet adapted to receive steam, said steam inlet positioned at 90° angle with the sample air inlet, the steam inlet having a steam outlet positioned such that the steam and the sample air flow in the same direction along the centerline of the enhanced apparatus.

The growth chamber for growth and activation of said aerosol particles has walls and is preferably a condenser.

The collection device for the activated aerosol particles disposed downstream of and in fluid communication with the growth chamber, has a nozzle means and a housing encapsulating the nozzle means, the housing having an impaction surface opposite the nozzle means, means for drawing sample air in communication with said housing, means adapted to receive carrier water and drain means.

Analytical means for measuring the chemical composition of the activated aerosol particles is disposed downstream and in fluid communication with the collection device.

The means for drawing sample air are connected to a vacuum source for directing the sample air carrying the activated aerosol particles through the nozzle means to form a jet stream, the jet stream impinging the activated aerosol particles upon the impaction surface.

The impaction surface has a groove along its perimeter, the groove adapted to receive wicking fibers forming a ring, wherein the wicking fibers are adapted to collect liquid from impacted aerosol droplets, which liquid is drained through the drain means of the housing.

The means adapted to receive carrier water are used for flushing the impinged activated aerosol droplets from the impaction surface into a liquid stream for transport to the analytical means.

The enhanced apparatus also includes an enhanced steam generating system including a steam saturator in fluid communication with the mixing chamber for providing steam to the second inlet of the apparatus, the saturator comprising a first stainless steal tubing adapted to receive a steady flow of purified water and a temperature controlled cartridge heater, the first tubing coiled around the cartridge heater, the first tubing adapted to receive a second tubing in fluid communication with the second inlet, the second tubing being bent such that the steam and the sample air flow in the same direction along the centerline of the apparatus.

In another aspect, the present invention provides a method for on-line measurement of chemical composition of aerosol particles which includes exposing aerosol carrying sample air to hot saturated steam, thereby activating the sample aerosol particles to droplets; collecting the droplets into a collection device for delivery as a jet onto an impaction surface, the impaction surface having a groove around its perimeter the groove adapted to receive wicking fibers; and flushing off the impacted droplets from the impaction surface to a drain for delivery to an analytical instrument for quantitative measurement.

In another aspect of the present invention, the collection device of PILS II can be used on stand-alone basis for the on-line measurement of chemical composition of cloud or fog particles. A method for measuring the chemical composition of cloud or fog particles using only the impactor portion of PILS II is also provided.

As a result of the present invention an enhanced apparatus and method are provided for rapid, on-line measurement of the ionic components of ambient aerosols. By utilizing the enhanced apparatus of the present invention the aerosol particle collection can be conducted at a higher sample flow resulting in minimal sample dilution and thus increasing the level of detection of the aerosol particles. The enhanced apparatus of the present invention is also more energy efficient because it can be passively air cooled and can be utilized in the absence of external cooling means.

Other improvements which the present invention provides over the prior art will be identified as a result of the following description which sets for the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTION OF THE DRAWINGS

FIG. 7 is a schematic diagram illustrating the use of PILS I-IC at the EPA Atlanta Supersite for rapid measurements of bulk aerosol ionic species.

DETAILED DESCRIPTION OF THE PREFERRED EMBODIMENTS

Particle-Into-Liquid Sampler I (PILS I)

Figure 1A:
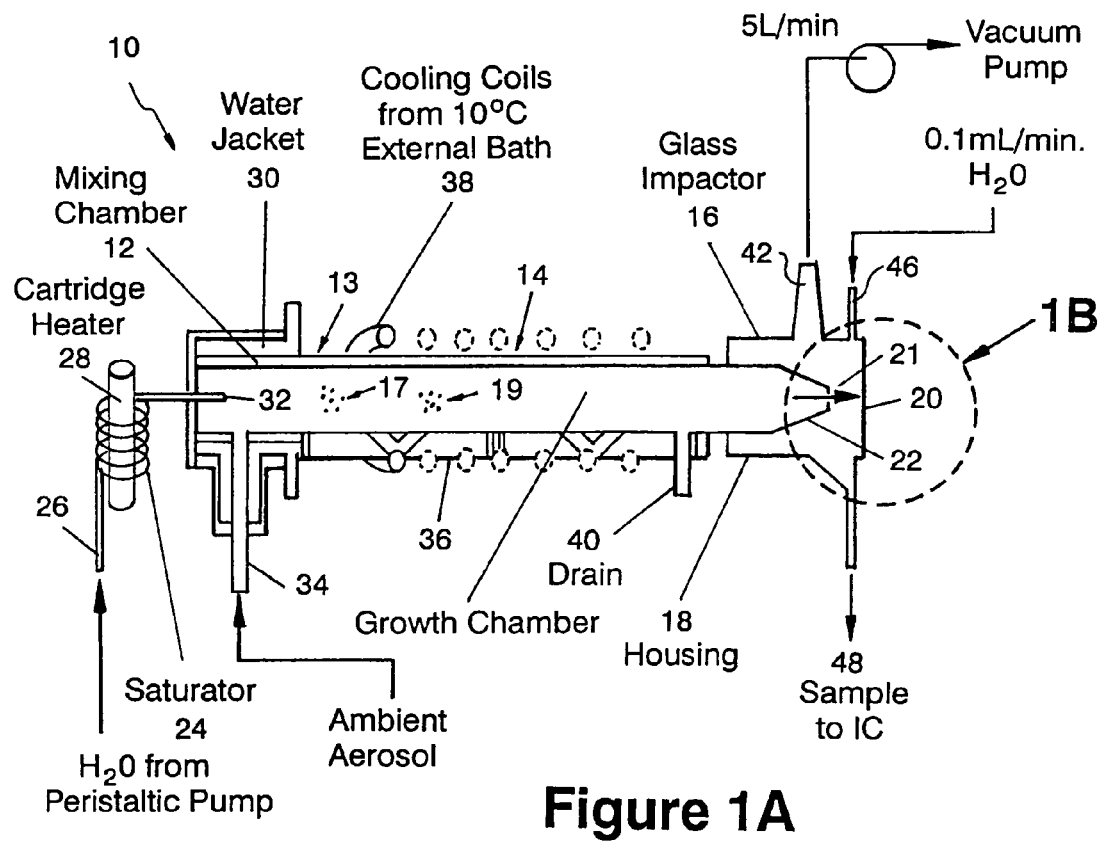
FIG. 1A is a schematic diagram of a particle-in-liquid sample (PILS I) collection apparatus for rapid measurement of aerosol bulk chemical composition.
Figure 1B:
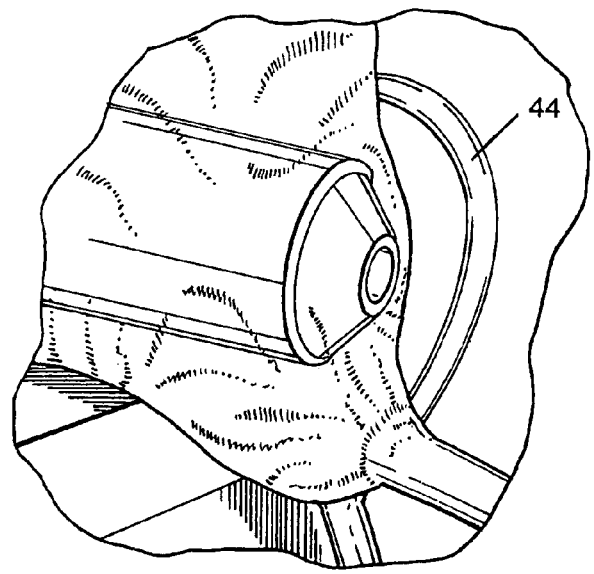
FIG. 1B is an insert showing with respect to PILS I the impactor nozzle, glass impactor housing, and stable liquid ring formed by the impinging air jet bearing activated aerosol particles onto the glass plate of the housing and a constant water flow flushing the aerosol particles off the glass plate.

Referring now to the drawings, FIG. 1a is a schematic diagram of a preferred embodiment of the apparatus of the invention showing a particle-into-liquid sample (PILS I) collector 10 for the rapid measurement of aerosol bulk chemical composition of activated aerosol droplets impacted onto a glass plate and carried by a flowing liquid stream for analysis by ion chromatography. The apparatus of the present invention comprises three main components: a mixing chamber 12 wherein sample air bearing aerosol particle is mixed with steam which condenses onto the incoming aerosol particles 17 to produce droplets bearing activated aerosol particles 19; a growth chamber 14 and a collection device 16.

As used herein "activated aerosol particles" refers to the fraction of aerosol particles entering the device that grow to large water droplets when mixed with saturated steam. The aerosol particles are then drawn into the growth chamber 14 which is disposed downstream of and in fluid communication with the mixing chamber 12 wherein the aerosol particles are allowed to grow to droplets having a diameter from about 1 micrometer to about 10 micrometers and preferably from about 2 micrometer to about 5 micrometer.

The activated aerosol particles are then collected by a collection device, preferably a single jet inertial impactor 16 which is used to collect droplets bearing the activated aerosol particles onto the vertical plate of a glass housing enclosing the inertial impactor from which the droplets are flushed off by a constant water carrier flow into a liquid stream for transport to an analytical tool.

A variety of analytical techniques can be employed to analyze the activated aerosol carrying liquid from the impactor/collector component. Useful techniques include, without limitation, ion chromatography, capillary electrophoresis, gas chromatography, high pressure liquid chromatography, total organic carbon analyzer, and liquid particle counters.

Particle Size Magnifier

The particle growth device used in the apparatus of the invention is a modified particle size magnifier (PSM) 13. To measure accurately the total bulk aerosol composition, a particle size magnifier must activate the aerosol particles comprising the majority of the total aerosol mass. These particles must grow to sizes that can be efficiently transported, yet easily captured by an inertial impactor 16. This requires activating all particles larger than approximately 80 nm diameter, and growing them to sizes on the order of a 1 to 10 micrometer diameter.

The particle size magnifier of the invention consists of the mixing chamber 12 and the growth chamber 14. The PSM grows particles in a supersaturated atmosphere created by adiabatic mixing of a hot saturated air stream with an ambient aerosol flow. The degree of supersaturation, which is controlled by the temperatures, saturation ratios, and mass flow rates of the hot and ambient air, determines minimum particle size activated and the amount of vapor available for condensation.

With further reference to FIG. 1A, the PILS I 10 further comprises a saturator 24 which produces steam required to activate and grow the fine aerosol particles present in the sample ambient air. Here, the saturator was a ⅛-inch stainless tube 26 through which a steady flow of purified water is pumped. This tubing was coiled around a temperature-controlled cartridge heater 28. The output of steam temperature and flow is controlled by changing the temperature and the water feed flow rate control. A water flow rate from about 0.4 mL min$^{-1}$ to about 0.5 mL min$^{-1}$ can be used to generate the steam when the sample air flow rate is 5 liter per minute. The steam was injected into the PILS I mixing chamber 12 through a first inlet 32 and immediately encountered the ambient air carrying aerosol particles 17 drawn in from the side through a second inlet 34 at a rate of 5 L min$^{-1}$. Rapid mixing of the hot saturated flow with the cooler aerosol flow created the supersaturated atmosphere needed for particle activation and growth.

To minimize potential volatility loss associated with altering the ambient aerosol temperature, sample air entering the mixing chamber 12 was held to near ambient temperature by a temperature controlled water jacket 30. To operate at higher flows, and for simplicity, the PSM mixer in a conventional device (Okuyama et al., 1984) was removed and the steam and ambient flows were directed at a 90° angle to each other, and neither flow was accelerated to promote turbulent mixing. This arrangement tended to limit activation to only particles larger than about 50 nm diameter. However, for urban environmental applications, this arrangement was found to be sufficient to capture most aerosol particles having a particle diameter of 2.5 micrometers, known as PM 2.5 mass (PM is particulate matter with a diameter less than 2.5 micrometers).

Following the mixing chamber 12, the supersaturated vapor and aerosol passed through a growth chamber 14 which was preferably a cylindrical condenser. The growth chamber/condenser could be from about 10 cm to about 20 cm long having an inside diameter about 2 cm and was kept at a temperature from about 5° C. to about 15° C. temperature. The condenser 14 was preferably a 16 cm-long tube with a wall temperature kept at 10° C. by a thermostated water jacket 36 consisting of cooling coils 38 surrounding the condenser 14. The residence time of the particles in this tube could be from about 0.25 seconds to about 0.75 seconds and was preferably approximately 0.6 seconds. The walls were cooled to maintain the supersaturation necessary for particle growth and yet remove as much water vapor as possible prior to the droplet collection region. This approach provides an important difference between our approach and other droplet growth devices. In other devices known in the art, much of the steam is condensed and added to the total sample liquid flow (Khlystov et al., 1995; Simon and Dasgupta, 1995). As a result in the devices known in the art, the condensed liquid dilutes the collected aerosol samples. Moreover, the amount of condensation is not constant so that the total volume of liquid varies and the resulting readings of activated aerosol content must be corrected. By contrast, in the present invention, we were able to control more effectively the total liquid stream containing the captured activated aerosol particles by separating the excess water vapor from the grown aerosol droplets. PILS I was operated with the growth chamber condenser 14 horizontal so that a drain 40 at the bottom of the condenser as shown in FIG. 1A could be used to remove the excess vapor as condensate from the walls. The horizontal arrangement has the potential disadvantage of losing large droplets to settling during transport. However, measurements indicated that particles in the condenser reached final diameters of nominally 2 to 3 micrometers, resulting in few particles lost by gravitational settling during transit through the condenser.

Inertial Impactor

With further reference to FIG. 1A, from the particle growth region the activated aerosol particles were carried by the flowing stream of sample air to an impactor/collection device 16. To collect the droplets into a flowing stream of water, sample air flow containing the activated aerosol droplets 19 was directed through the collection device, which is preferably a single circular nozzle impactor 16 which was designed for a 1 micrometer diameter cut size based on published impactor design criteria (Marple and Willeke, 1976; Rader and Marple, 1985). A jet 21 carrying activated aerosol droplets impinged onto a flat vertical glass plate 20. The vertical plate can be made of any inert material, such as glass, plastic or stainless steel and the like. It is preferable that the material be translucent, such as glass, in order to provide a visual checking of the operation of the system. The impactor nozzle 22 consisted of a 1.27 cm (0.50 inch) outside diameter (OD) stainless-steel or aluminum tube with 1.04 cm (0.41 inch) inside diameter (ID) that tapered down through a 45-degree angle to a nozzle diameter of 0.119 cm (3/64 in). Sample air was drawn through the PSM and impactor from a port 42 at the top of the impactor housing as shown in FIG. 1A. Droplets impacted onto the plate flowed radially out from the jet stagnation streamline, and at a diameter of roughly 1 cm, the liquid collected in an observable ring 44 as shown in the insert of FIG. 1B. As used herein, the jet stagnation streamline refers to an imaginary line which runs from the centerline of the jet nozzle perpendicular to and intersects the impaction plate at a point called the stagnation point. At the stagnation point the jet velocity is zero. Thus, on the impacting plate the air flowed radially away in every direction from the stagnation point. The shape of the liquid ring and its stability depended on the external dimension of the impactor nozzle 22, and the jet-to-plate distance. The latter was adjusted manually so that a stable ring was achieved. A peristaltic pump (not shown) was used to regulate the carrier water flow of 0.10 mL $min^{-1}$ introduced at the top of the ring through inlet 46. This flow drained down either side of the ring and allowed the collected drops to be flushed off the impaction surface. The resulting liquid containing the ambient activated aerosol particles flowed to a low point in the glass impaction-plate housing where it is continually pumped off to an analytical device. The liquid ring on the glass impactor surface provided a convenient visual gauge of the impactor operation; it showed that the liquid was not splashing and that a minimal wetted area was achieved, both of which were essential for a highly time resolved quantitative measurement.

Liquid Transport

The liquid sample collected at a base drain 48 of the impaction plate housing was pumped out at a rate faster than the rate at which it accumulated resulting in entrainment of air bubbles into the liquid stream. The bubble segments thus formed helped to minimize the axial mixing of the sample liquid during transport, thereby improving the time resolution of the analysis. Prior to injecting into the IC, the bubbles were removed by a debubbler (not shown in FIG. 1A) consisting of a glass tee in which the intersection was expanded to a volume of roughly 0.25 $cm^3$. The air bubbles, along with a small fraction of the sample liquid, were pumped off from the top leg, and the sample liquid, free of air, was transported to the IC at approximately 0.07 mL $min^{-1}$ from the bottom. This flow was then split and directed into two 150 μl sample-loops for injection into a duel channel ion chromatographer. The time to fill a sample loop is the integration time of the ambient air sample. With a liquid flow rate of 0.1 mL $min^{-1}$ through the sample loops, the time required to fill the sample loop was 4.3 minute integrated samples. In all cases, 0.159 cm (1/16 inch) OD Teflon tubing with 0.051 cm (0.02 inch) ID was used to transport the liquid. The small ID minimized the time for liquid transport from the aerosol collector to the IC sample loops.

Ion Chromatography Analysis

The concentrations of the major inorganic ionic components of the collected aerosol samples were analyzed using a computer-controlled dual channel ion chromatograph (Dionex, Model 300DX, Dionex Corporation, Sunnyvale, Calif.) which permitted both the cations and anions to be determined on-line and continuously. Each analysis channel consisted of a 6-port valve injector fitted with a 150 μL sample loop, a dual piston pump, an analytical separation column (IonPac CS12A, 4×250 mm, for cations; IonPac AS11, 4×250 mm, for anions, both from Dionex), a membrane suppressor, and a conductivity meter. The analysis was performed with isocratic elution using a 40 mN $H_2SO_4$ eluant for the cations and a 7.0 mN NaOH eluant for the anions, both at a flow rate of 1.0 mL $min^{-1}$. The analysis was automated using a computer interface (Dionex, Model ACI450) and the associated software running on a PC which controlled the sample injection, data collection, data storage and chromatographic analysis. This arrangement resulted in approximately 7-minute long chromatograms for both anions and cations. This 7-minute duty cycle was the limiting factor controlling the sampling frequency. The IC system was calibrated daily using standard solutions of four different concentrations of all the ions being analyzed.

In these instruments, the total sample liquid flow must be known to calculate the concentrations of the chemical components of the ambient aerosol. Although the carrier water flow rate was known, the amount of additional volume introduced by the collected water droplets was not directly measured. However, tests showed the final sample liquid flow remained fairly constant (±3%) for ambient aerosol concentrations ranging from 5000 to 10000 $cm^{-3}$, well within the range of ambient concentrations studied at the Atlanta EPA Supersite.

Measurement Uncertainties and Limit of Detection

The limit of detection (LOD) and uncertainty of the particle-into-liquid sample collector-ion chromatograph system (PILS I-IC) can be estimated from the expected sensitivity of the ion chromatograph (IC) and measured flow rates of the sample air and liquid stream. With an IC sensitivity of roughly 0.1 μM for nitrate, sulfate, sodium, ammonium, calcium and potassium, a sample flow rate of 5 L $min^{-1}$, a carrier liquid flow of 0.10 mL $min^{-1}$, the PILS I-IC was estimated to have a limit of detection near 0.1 μg $m^{-3}$ for these ionic components. The uncertainty associated with the mass measurements was estimated by combining the uncertainties in flow rates and IC calibrations. Uncertainties of both liquid and air flow rates were approximately ±4%. Uncertainties in the IC calibration for sulfate, nitrate, and ammonium were determined by comparisons with measurements of independent National Institute of Standards and Technology (NIST) traceable standards (Fisher Scientific). Comparisons immediately follow IC calibrations were within 3 to 5%, and 5 to 10% after running for an extended period. The overall uncertainty of the measured ionic species is estimated to be ±10%.

Particle Collection Efficiency

Figure 2:
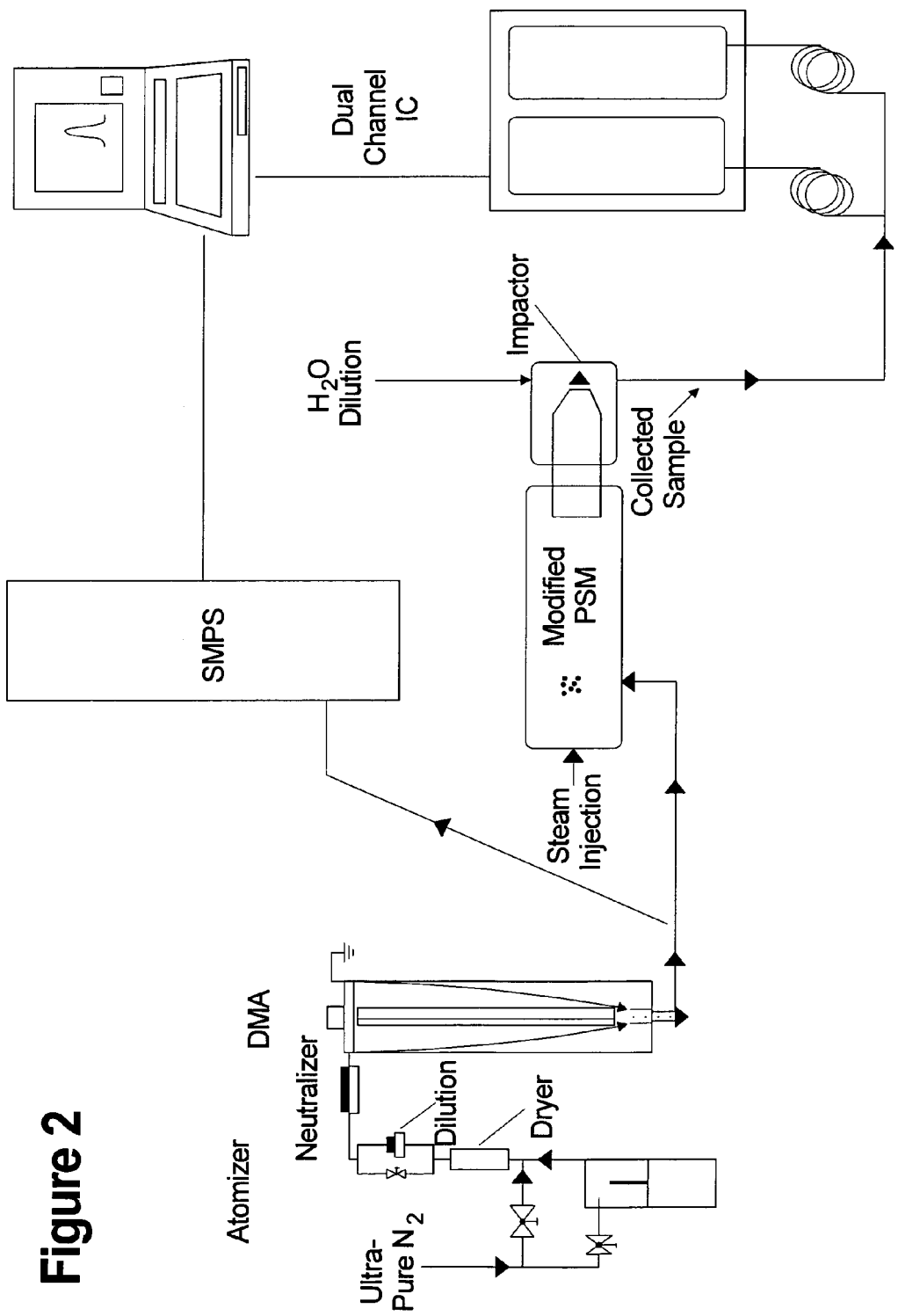
FIG. 2 is a schematic diagram of a system used for the calibration and mass collection efficiency of PILS I coupled to a dual ion chromatograph.
Figure 3:
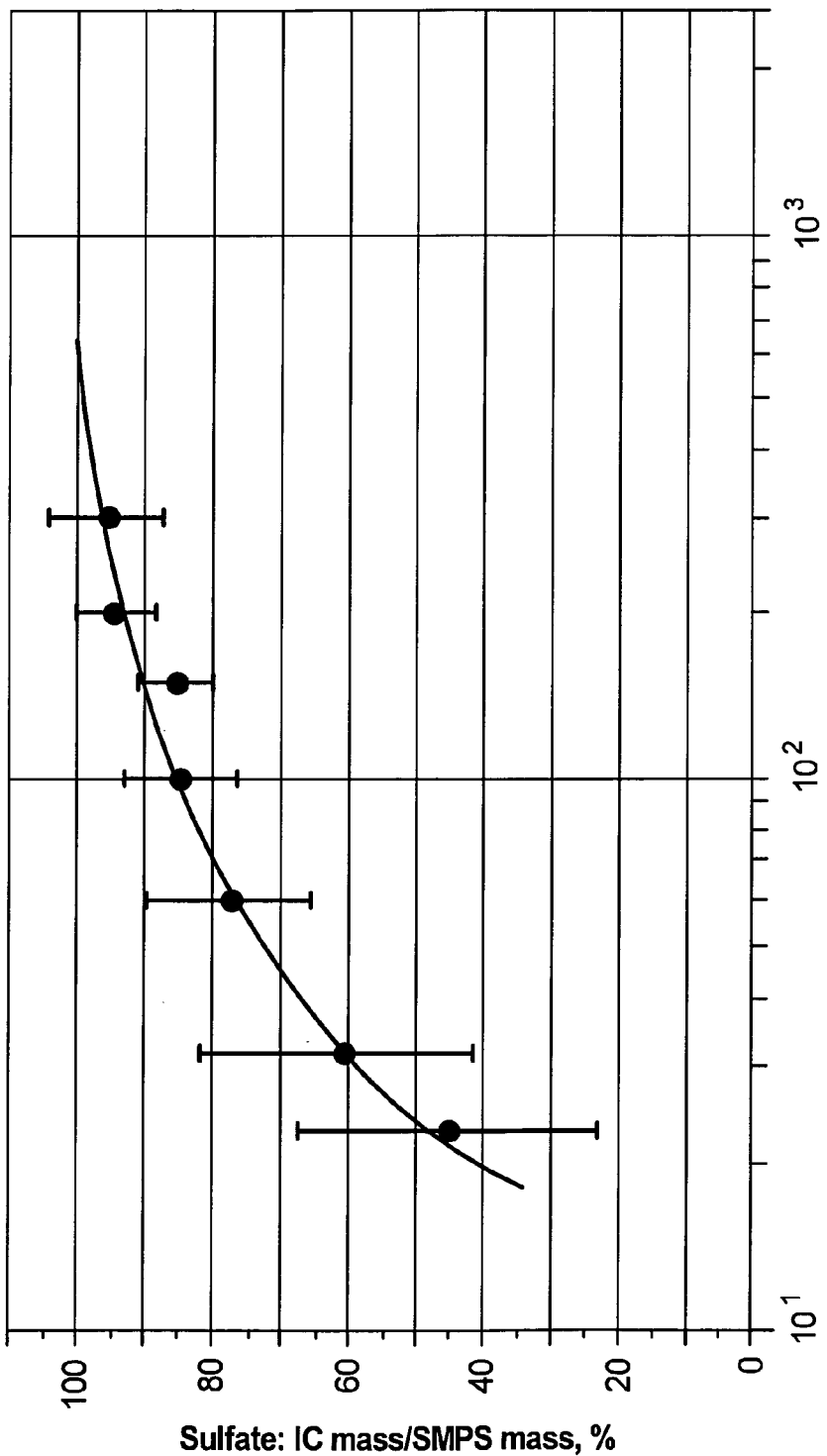
FIG. 3 is a graph illustrating results of the particle-in-liquid sample-ion chromatograph (PILS I-IC) mass collection efficiency tests for sulfate.

To determine the minimum size of particles activated, and the overall droplet transport and collection efficiency, the mass collection efficiency of PILS I was determined in the laboratory. In these calibration experiments, aerosol particles of known chemical composition and size were generated using the standard technique of atomizing an aqueous solution, neutralizing and diffusion drying the aerosol, and selecting a specific size with a differential mobility analyzer (DMA) (Knutson and Whitby, 1975) (FIG. 2). The mass concentration of the calibration aerosol was measured with the PILS I-IC and compared to the mass concentration measured with a scanning mobility particle spectrometer (SMPS) as provided by TSI Inc, St Paul Minn., (Wang and Flagan, 1990). It is noted that the SMPS measured the particle number distribution. This number was converted to total aerosol mass concentration from the known particle density and by assuming that the particles were dry. This was a valid assumption since the relative humidity (RH) of the calibration aerosol was about 20%, well below the efflorescence point of 40% RH for a calibration aerosol of ammonium sulfate (($NH_4)_2SO_4$). The SMPS measurement also accounted for single and multiple charged particle contributions to total mass. Calibration results for sulfate generated from $(NH_4)_2SO_4$ are shown in FIG. 3. Measured concentration ratios were compared to the size of the single charged particle generated. It is noted that at the smaller sizes where concentration ratios were sensitive to size, contributions of multiply charged particles to the total mass were small since most particles were singly charged. Selected calibration particle diameters ranged from 25 to 300 nm with total number concentrations varying between 150 and $10^5$ particles $cm^{-3}$, depending on particle size. These concentrations corresponded to sulfate mass concentrations between 0.5 and 40 μg $m^{-3}$, typical of ambient urban aerosol concentrations.

From FIG. 3, a maximum collection efficiency of 94% was measured, and over 80% of all particles larger than approximately 50 nm were collected. Below 50 nm, the collection efficiency dropped rapidly with decreasing size. The drop in collected mass efficiency was attributed primarily to non-activation of small size particles, a result of our limited mixing of saturated water vapor and sample air. It is noted that to achieve measurable masses for the smaller particle sizes tested (i.e., 25 micrometer diameter size), number concentrations of the order of $10^5$ particles $cm^{-3}$ were required. Since the activated drops grew to similar final sizes, during the experiments, there was a concern that unrealistically high concentrations necessary for the calibrations at the smaller sizes, could lead to underestimating the activation efficiencies due to vapor depletion. This was found, however, to have a minor effect since tests with increased steam-water flow rates had little influence on the lower size collection efficiencies. These tests demonstrated that the collection efficiency of PILS I was not significantly influenced by particle concentration for concentrations up to $10^5$ $cm^{-3}$.

Although the activation efficiency shown in FIG. 3 was likely sufficient for collecting most of the ambient aerosol mass in the EPA Supersite study, an enhanced mixer could be designed to activate much smaller particles.

Particle-Into-Liquid Sampler II (PILS II)

The present invention also provides an enhanced particle-into-liquid sampler, hereafter "PILS II" wherein the steam generation and sample air introduction system, the particle size magnifier and the droplet collector have been modified to enhance the aerosol particle collection at a higher sample flow while maintaining minimal sample dilution.

Figure 4:
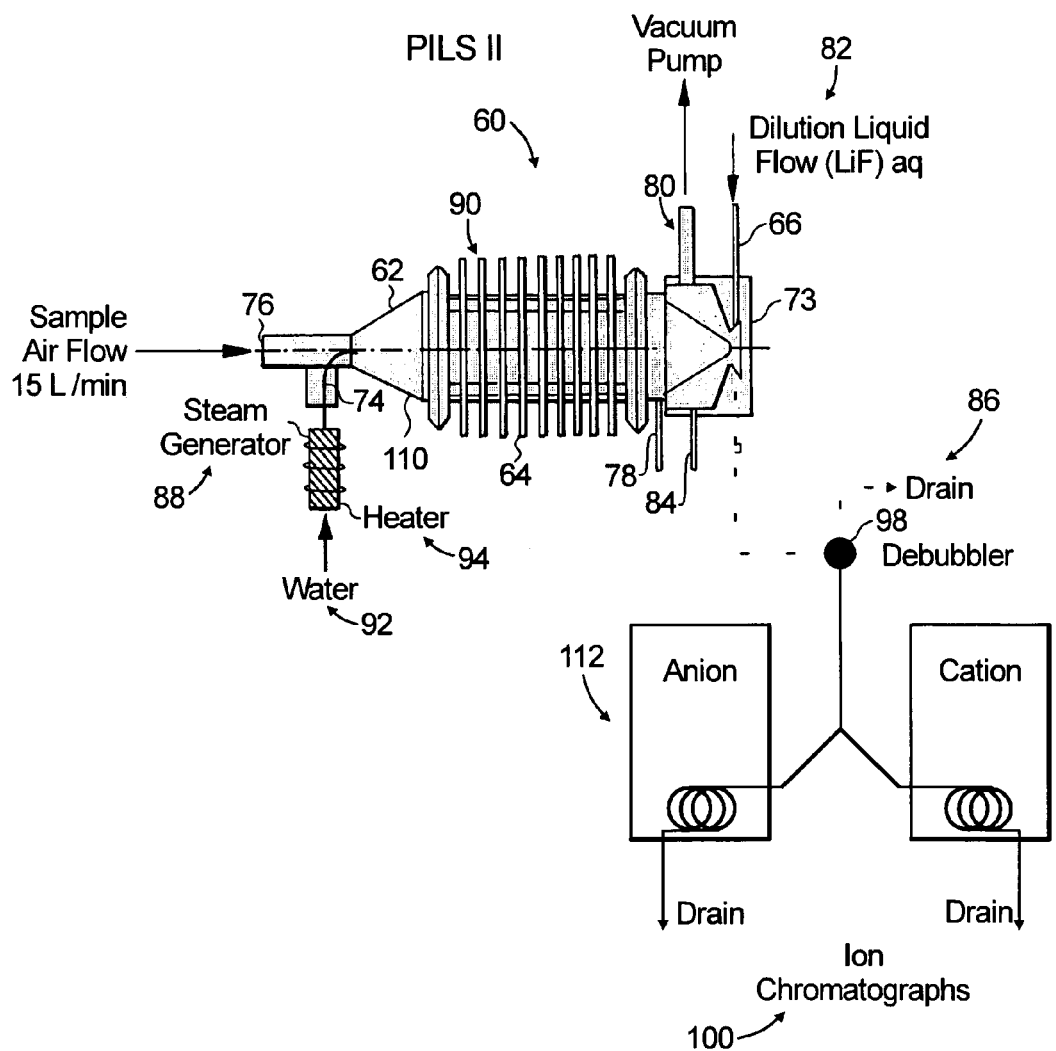
FIG. 4 is a schematic diagram of PILS II-IC system for rapid, on-line measurement of aerosol bulk chemical composition.

With further reference to the drawings, FIG. 4 is a schematic diagram of another embodiment of the invention showing PILS II-IC system having an apparatus 60 for the rapid, on-line measurement of aerosol bulk chemical composition of activated aerosol droplets and a cation/anion ion chromatograph 100.

The apparatus 60 shown in FIG. 4 comprises three main components: a mixing chamber 62 wherein sample air bearing aerosol particles is mixed with steam which condenses onto the incoming aerosol particles 110 to produce droplets bearing activated aerosol particles 112, a growth chamber 64 and a collection device 66. Incoming aerosol parties are drawn into the growth chamber 64 which is disposed downstream and in fluid communication with the mixing chamber 62, wherein the aerosol particles 110 come in contact with saturated steam and grow to droplets 112 having a diameter from about 30 nanometers to about 20 micrometers, and preferably to about 10 micrometers.

The activated aerosol particles are then collected by a collection device, preferably an inertial impactor 66 designed to concentrate the amount of activated aerosol particles present in the liquid stream used for transport to an analytical tool, such as for example, a cation/anion ion chromatograph 100.

The incoming aerosol particles grow in size and become activated in growth chamber 64. To produce the steam required to activate and grow the fine aerosol particles, a steam generator system is used.

The steam generator 88 consists of a 3.18 mm (⅛ in.) stainless steel tube 92 coiled around a temperature-controlled cartridge heater 94. A peristaltic pump (not shown) supplies 1.5 ml min$^{-1}$ of about 18.3 Mega Ohm deionized water to the cartridge heater to produce about 1.5 l min$^{-1}$ of steam. For aircraft operations, the peristaltic pump supplies 1.9 ml min$^{-1}$ of liquid steam-water to the cartridge heater 94. In order to achieve a steady jet of steam, the vapor is forced through a tube 74 which creates a back-pressure to suppress the sporadic boiling of the water. The tube 74 is about 5 cm (2 inches) long, has an outside diameter of about 1.58 mm (1/16 inches) and an inside diameter of about a 0.381 mm (0.015 inches). A 90° bend in tube 74 directs the steam along the centerline, parallel to the sample air flow 76. The small diameter of tube 74 provides the back-pressure necessary to achieve a steady steam flow and reduces heat transfer to the sample air and steam condensation prior to the injection into PILS II. The end of the steam tube is housed in a teflon sheath to further help reduce heat transfer to the sample and to hold a thermocouple (not shown) which monitors the steam temperature at the point of injection into the ambient air flow.

As distinct from PILS I, tube 74, a 1/16 inch tube injects the steam in the same direction as the sample air flow along the centerline of the apparatus 60. The use of tube 74 is essential to provide functions previously unavailable in PILS I, namely: (i) the narrow bore of tube 74 provides the back-pressure necessary to achieve a steady steam flow; and (ii) the small outside diameter (1/16 inch) reduces heat transfer to the sample air and condensation of the steam prior to injection into the PILS.

In PILS I the sample air flow turned a 90° bend within the instrument. By contrast, in PILS II the sample air flow comes in straight line along the center line of the apparatus 60 and the steam is injected inline with the sample air flow, near the apex of a conical expansion leading to the growth chamber 64. As a result of this modification it was possible to run the PILS II at 15 lpm versus 5 lpm for PILS I without significant losses to the lower limit of detection of the apparatus. This modification also made possible the measurement of aerosol particles up to 20 micrometer in diameter and preferably up to 10 micrometer.

Thus, as a result of the modification in steam generation and introduction into PILS II, it is possible to run the sampler apparatus 60 at increased sample flow from about 10 lpm to about 20 lpm, and preferably from about 15 lpm to about 17 lpm. Running PILS II at a higher sample flow also results in improvements in the lower limit of detection (LOD) of water soluble aerosol particles as discussed herein below.

Inside PILS II, the turbulent jet of steam mixes with the ambient sample at the apex of a conical expansion. The expanded wall reduces the flow velocity and allows for spreading of the steam jet to reduce the vapor loss by immediate condensation onto the walls of the apparatus 60.

Following the mixing chamber 62, the supersaturated vapor and aerosol particles passes through a growth chamber 64 which is preferably a cylindrical condenser. The growth chamber/condenser 64 could be from about 10 cm to about 13 cm having an inside diameter from about 4 cm to about 6 cm wide. The residence time of the charged particles in the condenser could be from about 0.8 seconds to about 1.2 seconds, preferably about 1 second. The residence time was sufficient for the particles to grow to a size larger than 1 μm.

Figure 5:
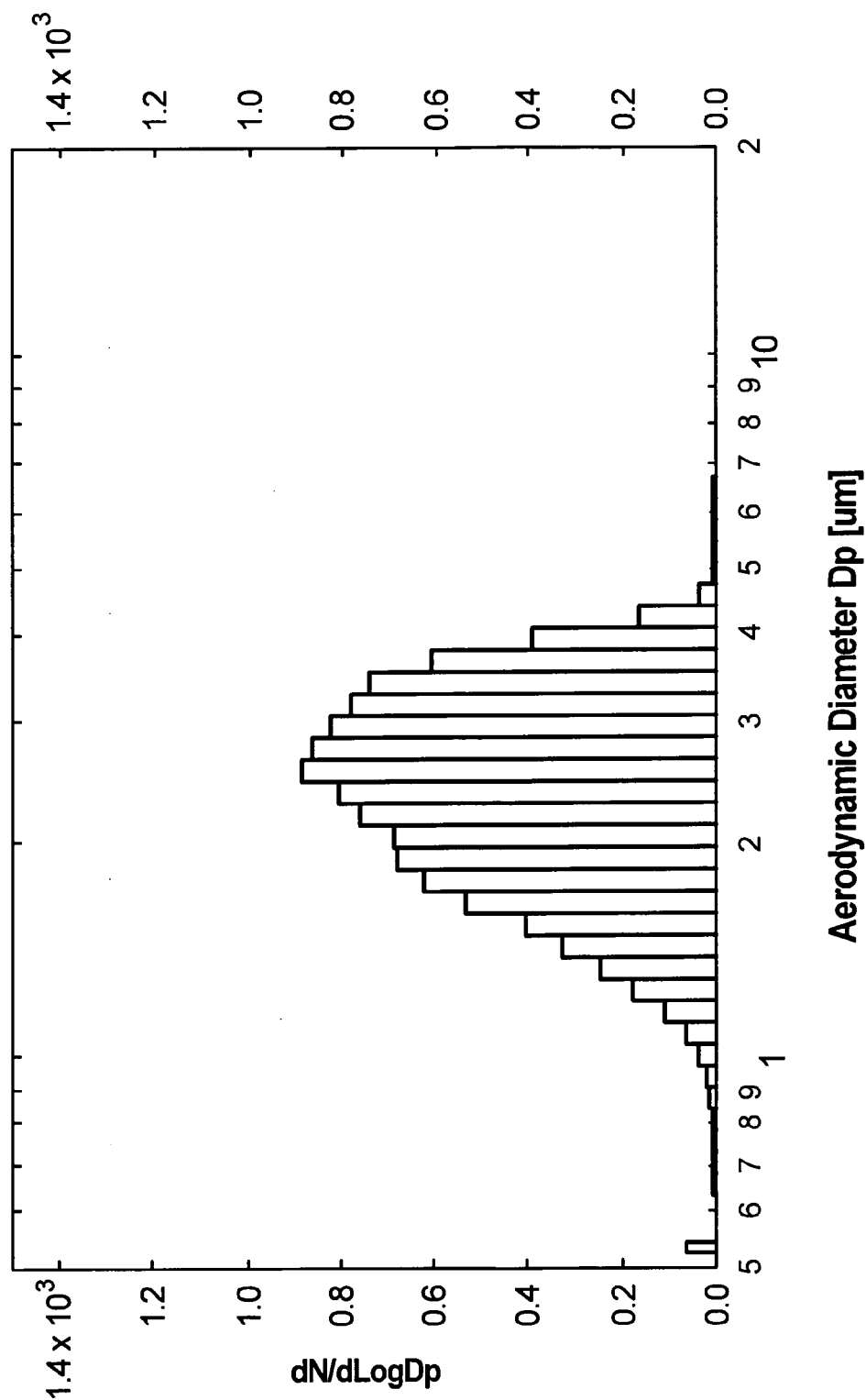
FIG. 5 is a block diagram showing the size distribution of droplets emerging from PILS II after sampling room air aerosols present in Georgia Tech laboratory.

The final particle size depended on the initial conditions (temperature and relative humidity) of the two merging flows and their mass flow rates. FIG. 5 shows a typical size distribution of droplets emerging from PILS II while sampling room air present in the Georgia Tech laboratory. The recorded data in FIG. 5 is a 10-second average measured with an Aerodynamic Particle Sizer (APS) (not shown) (APS, TSI, St. Paul, Minn.) attached to the end of the growth chamber 64.

With further reference to FIG. 4, the walls of the condenser were passively air cooled. The temperature of the condenser wall was close to room temperature. A finned sleeve 90 made of aluminum could be optionally used to dissipate heat by convection. Each fin can be about 4 inches in diameter in size. The finned sleeve 90 was optional since temperatures slightly above room temperature are also permissible.

The reduction in heat transfer to the sample air allows for additional simplifications to the growth chamber 64. While PILS I required an elaborate external cooling system, a water jacket around the mixing chamber and cooling coils for the growth chamber, PILS II does not require a cooling system. Indeed both the mixing chamber 62 and the growth chamber 64 of PILS II can be air cooled. Thus, the modification in the cooling of the mixing and growth chambers greatly simplifies PILS II since no expensive and cumbersome external cooling system is required. The modification of the growth chamber was also made possible by the enhanced inertial impactor described hereinbelow.

Inertial Impactor

Figure 6A:
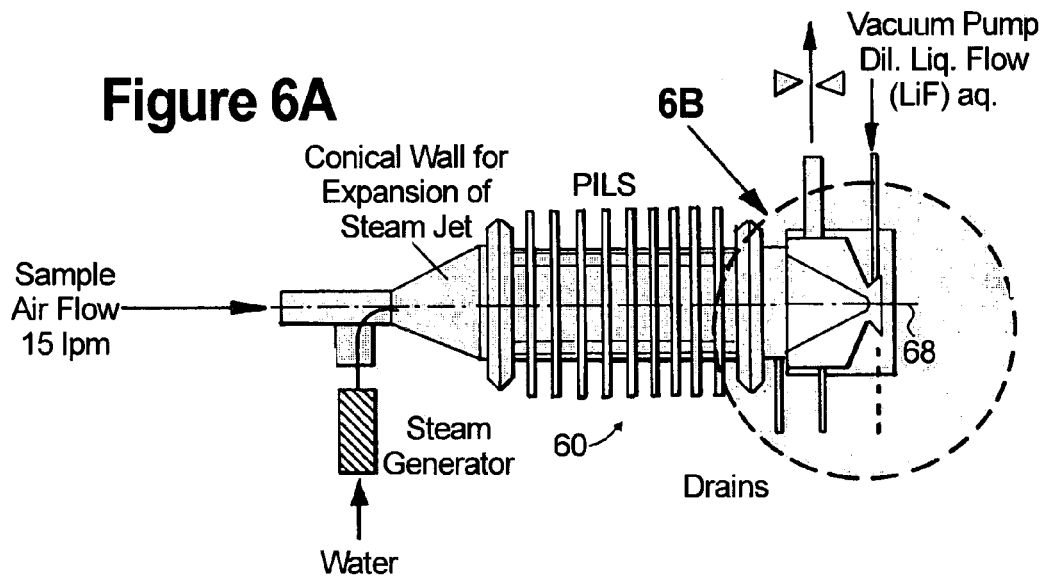
FIG. 6A is another schematic diagram of a PILS II apparatus.
Figure 6B:
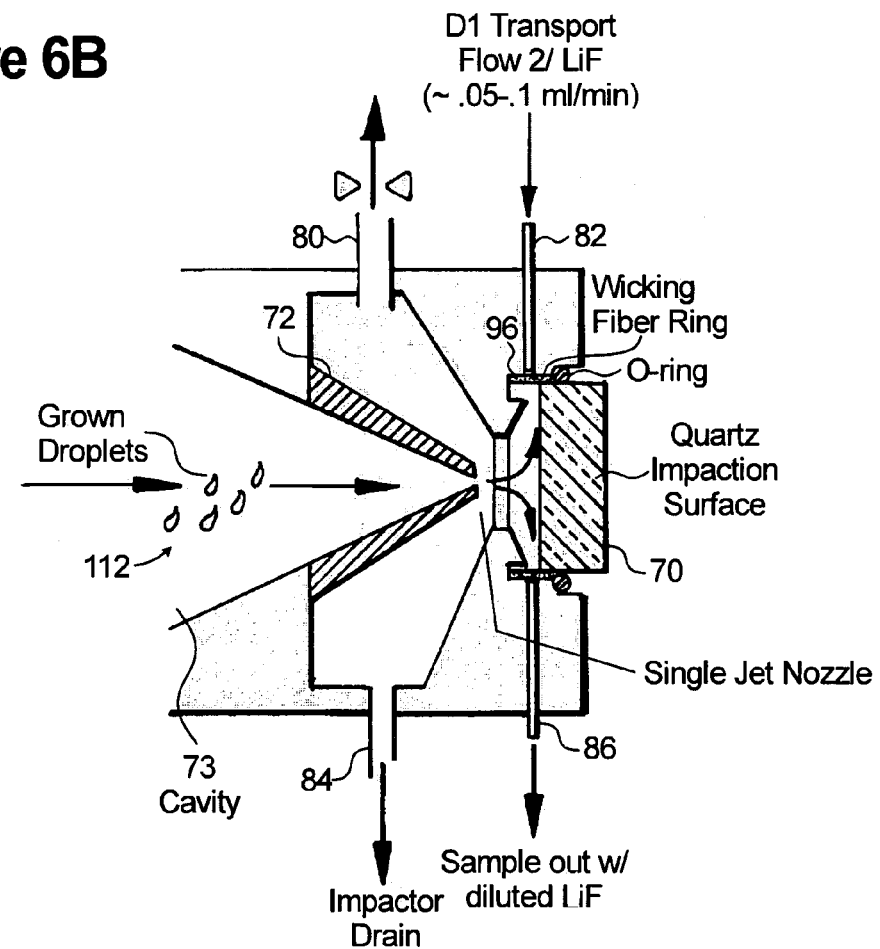
FIG. 6B is an insert showing details of the collection/impactor device.

With reference to FIG. 6A, from the particle growth region the activated aerosol particles 112 are carried by the flowing stream of sample air to an impactor/collection device 66. A schematic of the nozzle and impaction region of PILS II is shown in FIG. 6B. The aerosol particles are focused by a tapered wall into a nozzle means 72, the tip of which extended slightly into a conical-shaped cavity 73 of the impactor housing 68. In an embodiment, the impactor nozzle 72 tapers down to a tip containing a single orifice with a diameter sufficient to achieve a 1 μm cut size. The nozzle directs the sample flow containing the activated droplets against a flat surface 70 inside the cavity to achieve a 1-μm diameter cut size based on published inspection design criteria. (Marple and Willeke, 1976; Rader and Marple, 1985). The housing 68 can be made of any plastic or metal material such as, for example, polycarbonate (lexan) or stainless steel. The housing 68 contains nozzle means 72, a vertical flat surface 70 directly across from the nozzle means 72, and a groove around the perimeter of surface 70, the groove for receiving ring means 96. The vertical flat impactor surface 70 can be a quartz disc pressed into the impactor body. The vertical flat impactor surface 70 is perpendicular to the jet stagnation streamline. The jet stagnation streamline has the same meaning described in connection with PILS I.

The radially spreading jet of air forces the impacted droplets to the perimeter of the impactor surface 70. The impactor surface can be a plate preferably round in shape, such as a disc having a diameter of about 0.633 inches made of an inert, preferably transparent material, such as, for example, quartz. A quartz plate is preferred because it is chemically inert, highly wettable, and allows viewing of the impacted drops.

With further reference to FIG. 6B along the perimeter of the impaction plate 70, a groove (not shown) was machined in the impactor housing, the groove adapted to receive quartz fibers. The groove is preferably ring shaped and is placed along the perimeter of the impaction surface 70. Quartz fibers can fit into the groove to form a ring 96 having a diameter of 0.633 inches. The ring can be made of quartz fibers or other material such as stainless steel wire mesh having a wicking action. Ring 96 serves to collect the liquid from the impacted droplets, limits dispersion of the transport flow, and conducts the combined flow to drain 84 at the bottom of the housing conical cavity 73. Quartz fibers or stainless steel wire mesh placed in the groove around the perimeter of the impaction surface 70 have a wicking action and can wick away the liquid from plate 70 as soon as it reaches the perimeter of ring 96 and thus, are also referred to herein as "wicking fibers".

With further reference to FIG. 6B, the impactor nozzle 72 consisted of a 0.59 cm (0.2 inches) outside diameter (OD) machined aluminum part that tapered down through a 20 degree angle to a nozzle having an inside diameter of 0.089 inch. The impactor nozzle 72 can also be made of any machinable material, such as stainless steel or aluminum. Sample air was drawn through the particle size magnifier (PSM) and impactor from a port 80 positioned at the top of the impactor housing as shown in FIG. 6B.

As with other enhancements present in PILS II, changes made to the inertial impactor resulted in a significant improvement in droplet collection by comparison to PILS I. In PILS I the impactor was a flat glass plate. In PILS I a significant amount of water vapor that existed in the growth region condensed on the impactor plate along with the captured droplets that contain the species to be measured, and the combined flow was collected at the bottom of the impactor. Extensive cooling in the growth region was necessary to minimize the contribution of vapor condensate on the impaction plate and thus minimize dilution of the liquid containing the aerosol constituents to be detected. By contrast, the impactor of PILS II can separate more effectively the wall condensate and the collected droplets, concentrating the liquid supplied to the IC, and improving the LOD of the method when IC sample loops are employed.

When operating, air containing the grown aerosol particles impinged onto the quartz surface 70 where the aerosol particles impact. Liquid from these captured aerosol particles was pushed to the perimeter of the quartz plate 70 by the radial spreading air jet and merged with the transport flow introduced through the top of the conical-shaped housing cavity 73. The combined flow was drawn out from the bottom of the conical cavity 73. Outside the cavity, yet within apparatus 60, the surface of the impactor body is angled away from the cavity so that water vapor condensed on the tilted surface flows away and out of the impactor through a drain line. In this way, the wetted area where the sample was collected was minimized and most of the excess condensed water was separated from the liquid containing the dissolved aerosol species. The volume of liquid collected from the collection device 66, and hence sample-dilution, can be adjusted through selection of the transport flow.

As a result of enhancements made in the design of the inertial impactor, PILS II can collect droplets at rates much higher than 5 lpm, the limit that could be reached with PILS I. For example, the enhanced collector of PILS II, can now collect droplets at rates higher than 7 lpm and preferably in a range from about 10 lpm to about 20 lpm. A higher sample flow rate increases the mass of collected aerosol particles resulting in improved LOD and a faster instrument response. This characteristic is especially important when measuring low concentrations of aerosol particles such as are found in an aircraft or in remote areas.

In another aspect, the inertial impactor/collection device 66 can be utilized for stand-alone applications such as, for example, on-line measurement of chemical composition of cloud or fog particles captured from an aircraft or on the ground. Cloud or fog aerosol particles are naturally laden with moisture and do not require activation by condensation with steam as occurs in PILS I or PILS II. When utilized as a stand-alone collection device, the impactor can collect droplets having a diameter from about 10 micrometers to about 50 micrometers. The incoming sample air flow can vary in a range from about 7 lpm to about 30 lpm.

For stand alone use the collection device 66 has all the components shown in FIG. 6B except that the impactor 66 is not in fluid communication or otherwise connected to growth chamber 64. As shown in FIG. 6B, when used in stand-alone mode, the impactor 66 includes housing 68, nozzle means 72 and a flat vertical surface 70 directly across from the nozzle means 72. The flat surface is preferably a disc having a groove around its perimeter, the groove adapted to receive wicking fibers 96.

When operating in a stand-alone mode the impactor collects cloud or fog particles directly from clouds or fog through nozzle means 72. The means for drawing sample air 80 is connected to a vacuum source as shown in FIG. 6B. When the vacuum is operating the cloud or fog particles are directed through nozzle means 72 to form a jet stream that impinges the cloud or fog particles upon the impaction surface 70. The impaction surface 70 has a groove around its perimeter adapted to receive wicking fibers 96 in the groove. The liquid transport system connecting the cloud and fog particles to the analytical means is the same as that used for PILS II as described in more detail below.

With reference to FIG. 4 the liquid transport system for PILS II includes a drain 84, a sample exit tube 86 and a debubbler 98. The liquid sample collected at a base drain 84 of the impactor housing 68 was pumped to a debubbler 98. A small selectable flow of high purity deionized water 82 introduced at the top of the conical cavity 73, travels along the fiber ring 96 and transports the collected liquid to an exit tube 86 at the base of the impactor housing 68 to the debubbler 98. The debubbler 98 can be a glass tee in which the intersection was expanded to a volume of agent 0.25 cm$^3$. The air bubbles, along with a small fraction of the sample liquid, were pumped off from the top leg, and the sample liquid, free of air, was transported to the IC at approximately 0.07 mL min$^{-1}$ from the bottom. This flow was then split and directed into two 150 µl sample-loops for injection into a duel channel ion chromatographer. The time to fill a sample loop is the integration time of the ambient air sample. With a liquid flow rate of 0.1 mL min$^{-1}$ through the sample loops, the time required to fill the sample loop was 4.3 minute integrated samples. In all cases, 0.159 cm (¹⁄₁₆ inches) outside diameter PEEK™ polymer tubing with 0.059 cm (0.02 inch) inside diameter was used to transport the liquid.

Measurement of Ambient Aerosol Concentration

In the final exiting flow 84, in addition to liquid from the droplets diluting the sample of aerosol particles, a small amount of water condensed out of the saturated air passing over the cooler quartz impaction surface. To account for this dilution, the incoming transport flow is spiked with a known concentration of lithium fluoride or related non-interfering ions. By measuring the diluted lithium and/or fluoride exiting the impactor, the added water can be taken into account and the measured aerosol concentration can be calculated by the following equation:

$$[C_g] = [C_L] q_{in} R/Q_a \qquad (1)$$

where:
- [$C_g$] is the ambient aerosol concentration ($\mu g\ m^{-3}$);
- [$C_L$] is the concentration of the ion in the collected sample liquid ($\mu g\ l^{-1}$) for ion chromatographic analysis, [$C_L$] is determined from calibrations with NIST-traceable ion standards in aqueous solutions, wherein NIST is National Institute Of Standards and Technology;
- $q_{in}$ is the flow of the spiked transport liquid entering the top of the impactor ($\mu g\ l^{-1}$); typically $q_{in}$ is 0.05 to 0.1 ml min$^{-1}$;
- R is the ratio of the spiked species concentration (e.g. Li$^+$) entering the impactor divided by the concentration exiting the impactor; this ratio accounts for the aerosol sample dilution.
- $Q_a$ is the volumetric flow rate of sample air entering the PILS I or PILS II (1 min$^{-1}$).
   For PILS I $Q_a$ is about 5 L/min and for PILS II $Q_a$ is about 15 L/min.

Ion Chromatography

To a large extent, the analytical technique determines both the sampling rate (i.e., duty cycle) at which species can be detected, and the lower detection limits. Ion chromatography (IC) has been the primary means of online analysis of the sample flow because it allows for quantitative speciated inorganic and organic analysis depending on the type of separation column used. A Metrohm IC (Compact 761, Metrohm, Herisau, Switzerland) was chosen for its simplicity, compactness, and adaptability in the field. The instrument has also proven reliable in continuous monitoring.

Figure 9:
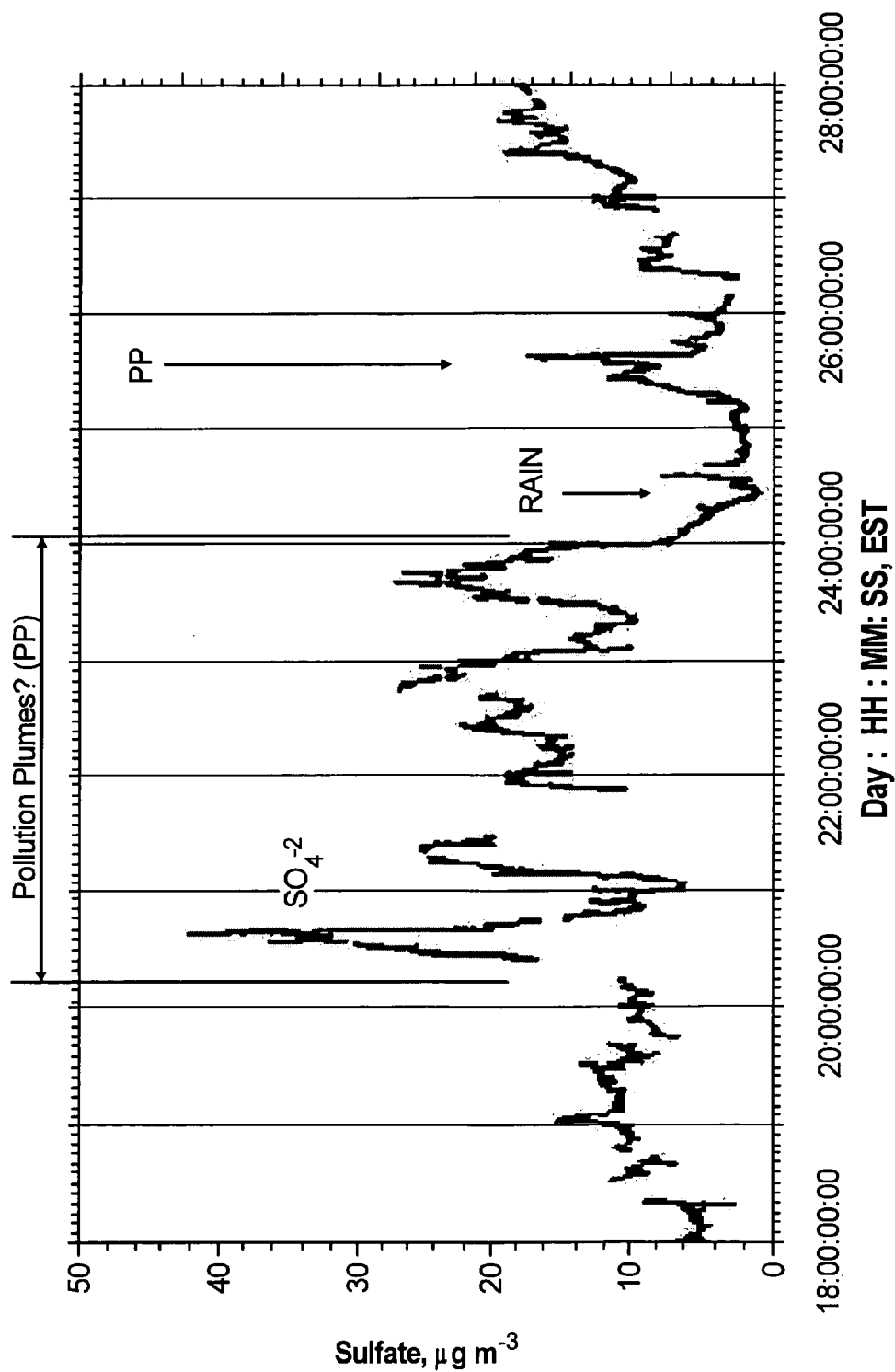
FIG. 9 is a graph illustrating PILS I-IC measurements of sulfate ($SO_4^{-2}$) measured at the EPA Atlanta Supersite.

The underlying limitation in the sampling rate of the PILS II-IC system is determined by the duty cycle of the IC, or the ability of the column to adequately separate the species of interest. The trade off with IC analysis is between the number of analytes eluted and sampling time. Ion chromatography is often not a fast analysis technique, however selection of appropriate columns and eluants has enabled sampling rates of the major ions as fast as 3.5 minutes. Table 1 below summarizes combinations of columns and eluants that were used in ground-based and aircraft studies.

the IC, which in turn constrained the selection of sample loop volume and flow rate of liquid generated by the PILS II as related to $q_{in}$. In recent aircraft studies, for example, separation of major inorganic ions was possible within 4 minutes using a 150 μl sample per loop and a transport liquid from $q_{in}$ of approximately 0.1 ml min$^{-1}$, which was split between two ICs as shown in FIG. 9. In ground-based studies, where speciated organic acids were desired, 150 to 500 μl sample loops were used and filled within 15–30 minute duty cycles using various $q_{in}$. Based on ambient measurements of 3 times the standard deviation of baseline, the limits of detection (LOD) were approximately 50 ng m$^{-3}$ and 10 ng m$^{-3}$ for the cation and anion species, respectively. The higher cation LOD is due to a non-suppressed cation IC (Metro Compact IC 761).

EXAMPLES

Example 1

Results from the Atlanta EPA Supersite Study for PILS I

PILS I was tested during 1999 at the Atlanta EPA Supersite experiment where a large assembly of aerosol equipment was being tested for their performance. As the first EPA Supersite, our experiments were aimed at intercomparing various techniques for measuring chemical composition of particles smaller than 2.5 micrometer diameter, so-called PM2.5. A secondary goal was to study the chemical and physical properties of urban PM2.5 aerosol particles in the southeastern United States. Preliminary results showed that the PILS agreed well with other semi-continuous techniques, and were in general agreement with filter measurements of non-volatile species, such as sulfate.

The particles bearing diameter less than 2.5 micrometer (PM2.5) for sampling system, including the PILSI-IC, are shown in FIG. 7. The sampling inlet consisted of an inverted stainless steel tube connected to a 10 L min$^{-3}$, 2.5 microme-

TABLE 1

Combinations of columns and eluants to measure specific ions in the PILS liquid.

| | Column | Eluant | Ions | Time Eluted [min.] | Sample loop volume [μl] |
|---|---|---|---|---|---|
| Anions | Metrosep Supp 5-100 × 4.0 mm | Carbonate/ Bicarbonate | Cl$^-$, NO$_3^-$, SO$_4^{-2}$, HPO$_4^{-2}$, NO$_2^-$ | 3.5–4 | 150 |
| | Supp 5–250 (+Star Anion) | 5 mM Carbonate/ 1 mM Bicarbonate | Cl$^-$, NO$_3^-$, SO$_4^{-2}$, HPO$_4^{-2}$, NO$_2^-$, Acetate, Formate, Oxylate, Methane Sulfonic Acid | 15(30) | 500 |
| Cations | Metrosep Cation 1–2 | L-Tartaric/ Dipicilinic Acid | Li$^+$, Na$^+$NH$_4^+$, K$^+$, Ca$^{+2}$, Mg$^{+2}$ | 3.5–4 | 150 |
| | Metrosep Cation 2 100 B-100 × 4.0 mm-7 um | Dipicolinic/Nitric/ Acetronitrile | Li$^+$, Na$^+$NH$_4^+$, K$^+$, Ca$^{+2}$, Mg$^{+2}$ | 15 | 500 |
| | Metrosep Cation 2 100 | 2.5 mM MSA | Li$^+$, Na$^+$NH$_4^+$, K$^+$, Ca$^{+2}$, Mg$^{+2}$ | 15 | 500 |

For the sake of simplicity and robust field operation, sample loops were used to collect the liquid for IC injection versus concentrator columns, as was done in other techniques As shown in Boring et al., 2002; Slanina et al., 2001. The volume of the injected sample represented the average chemical composition during the time of filling. Between injections, the fill-time was constrained by the duty cycle of ter cut URG (University Research Glass) cyclone to permit measurements of PM2.5. Inside the sampling trailer, the 10 L min$^{-3}$ aerosol flow passed through two URG annular denuders in series, one coated with citric acid and the other calcium carbonate, to remove gaseous NH$_3$, and SO$_2$ and HNO$_3$ respectively. The denuders were regenerated approximately every 2 days.

Figure 8:
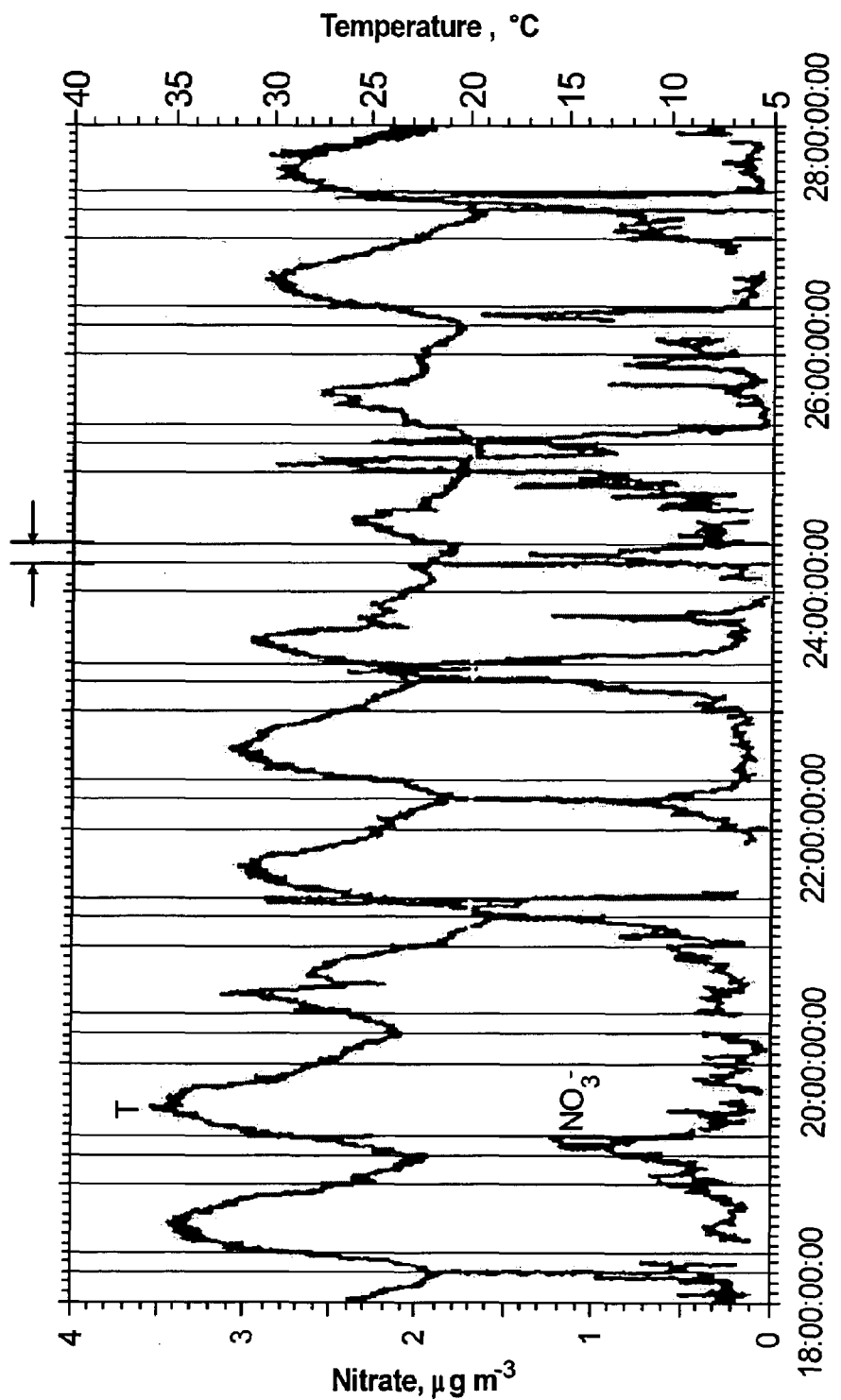
FIG. 8 is a graph illustrating PILS I-IC measurements of nitrate ($NO_3^-$) and temperature (T) measured at the EPA Atlanta Supersite.
Figure 10:
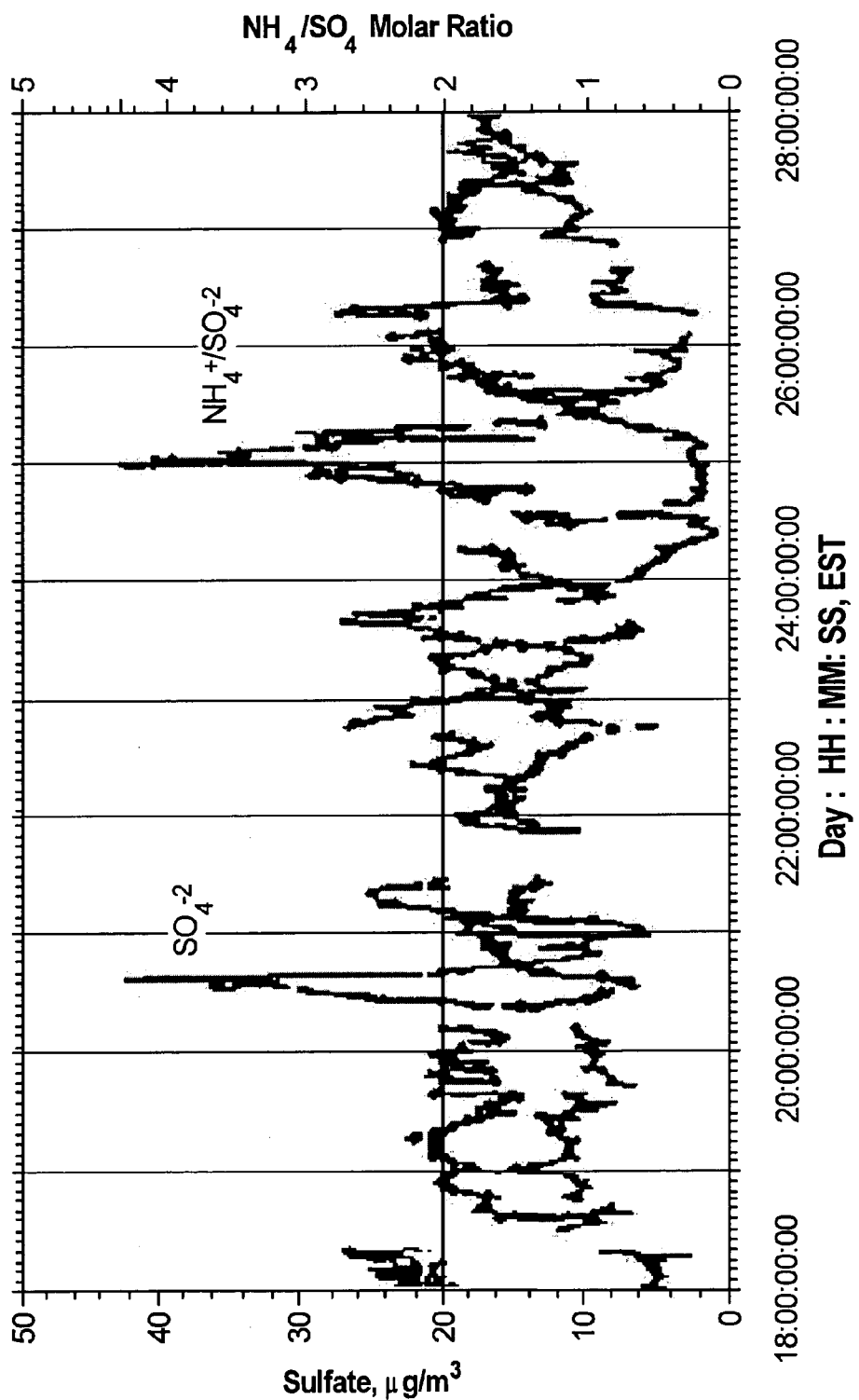
FIG. 10 is a graph illustrating PILS I-IC measurements of sulfate ($SO_4^{-2}$) concentrations and ammonium to sulfate molar ratios ($NH_4^+/SO_4^{-2}$) measured at the EPA Atlanta Supersite.

Focusing on nitrate, sulfate, and ammonium, FIGS. 8, 9 and 10 show the data collected during a 10-day sample period, from Aug. 19 to Aug. 28, 1999. FIG. 8 shows nitrate levels ranging between roughly the LOD of the system, i.e., 0.1, to 3.0 µg m$^{-3}$ during this time. The nitrate measurements demonstrate how highly time-resolved measurements could provide insights into processes controlling the massloadings and chemical compositions of ambient aerosol. FIG. 8 shows that on practically every day, nitrate peaked in early morning between 600 and 1000 Eastern Standard Time. Although this coincides with the morning rush hour, peaks were also observed on Saturday and Sunday when there is no rush hour traffic. These peaks correlate with periods of minimum daily temperatures, which are also times of maximum relative humidity. It is known that partitioning of nitric acid between the gas and condensed phase is highly sensitive to temperature, RH, and aerosol composition. Consistent nitrate peaks following minimum temperatures and maximum daily RH indicate that these thermodynamic effects played a major role in the formation of the early morning nitrate peaks.

During the period of August 18 to August 28, other ancillary measurements showed that total PM2.5 mass concentrations varied between 5 to 50 µg m$^{-3}$ as measured by the tapered element oscillating microbalance instrument ("TEOM") with inlet heated to 50° C., as provided by Rupprecht and Patashnick Co., Albany N.Y. (Bergin, personal communication). As is typical of the eastern United States, sulfate was found to be a major component and nitrate a minor component of the total PM2.5 aerosol mass. FIG. 9 shows the sulfate concentration measured during this period. Sulfate concentrations ranged from about 2 to 40 µg m$^{-3}$, with highest levels corresponding to pollution episodes, possibly associated with power plant plumes or other local sources. During this period these plumes were observed primarily between August 20 to August 24.

Figure 11:
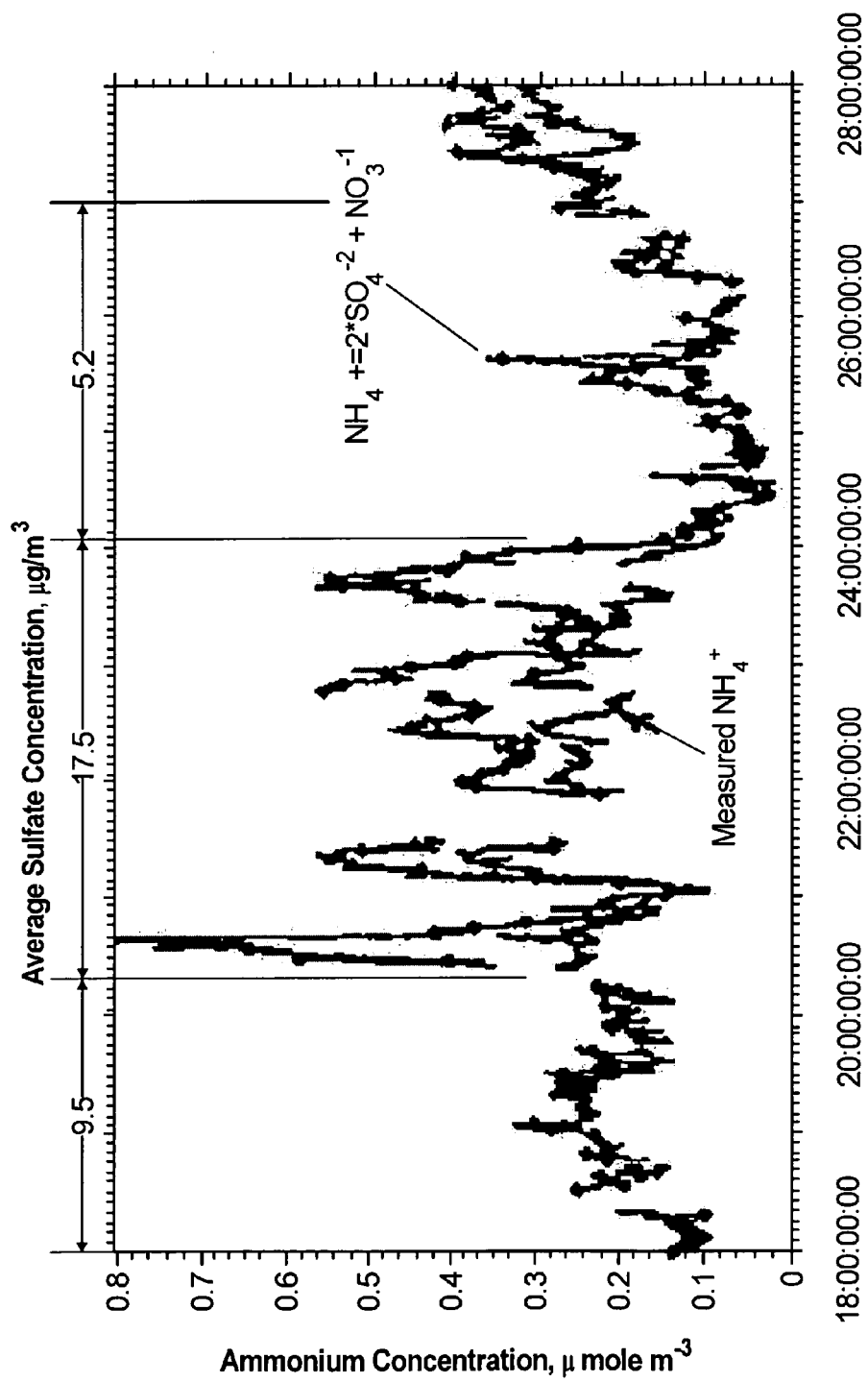
FIG. 11 is a graph illustrating PILS I-IC measurements of the ammonium ion ($NH_4^+$) molar concentration and the calculated ammonium molar concentration necessary to neutralize the measured aerosol sulfate ($SO_4^{-2}$) and nitrate ($NO^-_3$) at the EPA Atlanta Supersite.

Sulfate concentration and ammonium to sulfate molar ratios are plotted in FIG. 10. The molar ratios are of interest since they provide insights into aerosol gas-to-particle conversion processes and also served as an internal check on our measurement accuracy. Under typical conditions, ammonium to sulfate molar ratios were near two, suggesting that sulfate was usually completely neutralized, assuming most of the ammonium was associated with sulfate. However, during pollution episodes, molar ratios often dropped below one, arising most likely from the fact that the available ammonia present was insufficient to neutralize the unusually large amount of sulfuric acid produced in the plume. There were also periods when molar ratios exceeded two. These typically occurred when the total aerosol mass concentrations were very low. For example, molar ratios peaked near 4 during periods near midnight on August 26 and August 27. During these times PM2.5 levels were unusually low at 10 µg m$^{-3}$. At these times ammonium may also be associated with other acidic species such as nitric acid. To test this we plotted in FIG. 11 the measured ammonium molar concentration and the concentration calculated from measured sulfate and nitrate, assuming that these acidic species are completely neutralized by ammonium. The graph shows that the measured and calculated ammonium concentrations agree remarkable well, except under high sulfate concentrations associated with pollution plumes. During these times there appears to be insufficient ammonia to neutralize the aerosol. These data attest to the accuracy of the independent anion and cation measurement results.

Our preliminary investigations with PILS I coupled with an ion chromatograph (IC) suggest that it is a powerful tool for rapid quantitative measurements of aerosol particle ionic composition. The instrument is simple and robust. Sampling artifacts associated with filter techniques are minimized since particles are rapidly stabilized by formation of water drops collected into a flowing liquid. Data is obtained near real-time with a 4.3 minute integrated sample at a duty cycle of 7 min. With an IC sensitivity of roughly 0.1 µM, a sample flow rate of 5 L min$^{-1}$, collecting particles into a liquid flow of 0.10 mL min$^{-1}$, the PILSI-IC had a limit of detection near 0.1 µg m$^{-3}$ for nitrate, sulfate, sodium, ammonium, calcium and potassium. Although, at this point we have only focused on coupling the. PILS I to an IC, other analytical techniques could also be employed to measure quantitatively additional aerosol components and properties.

Example 2

Calibration Results of Particle Collection Efficiency for PILS II

Figure 12:
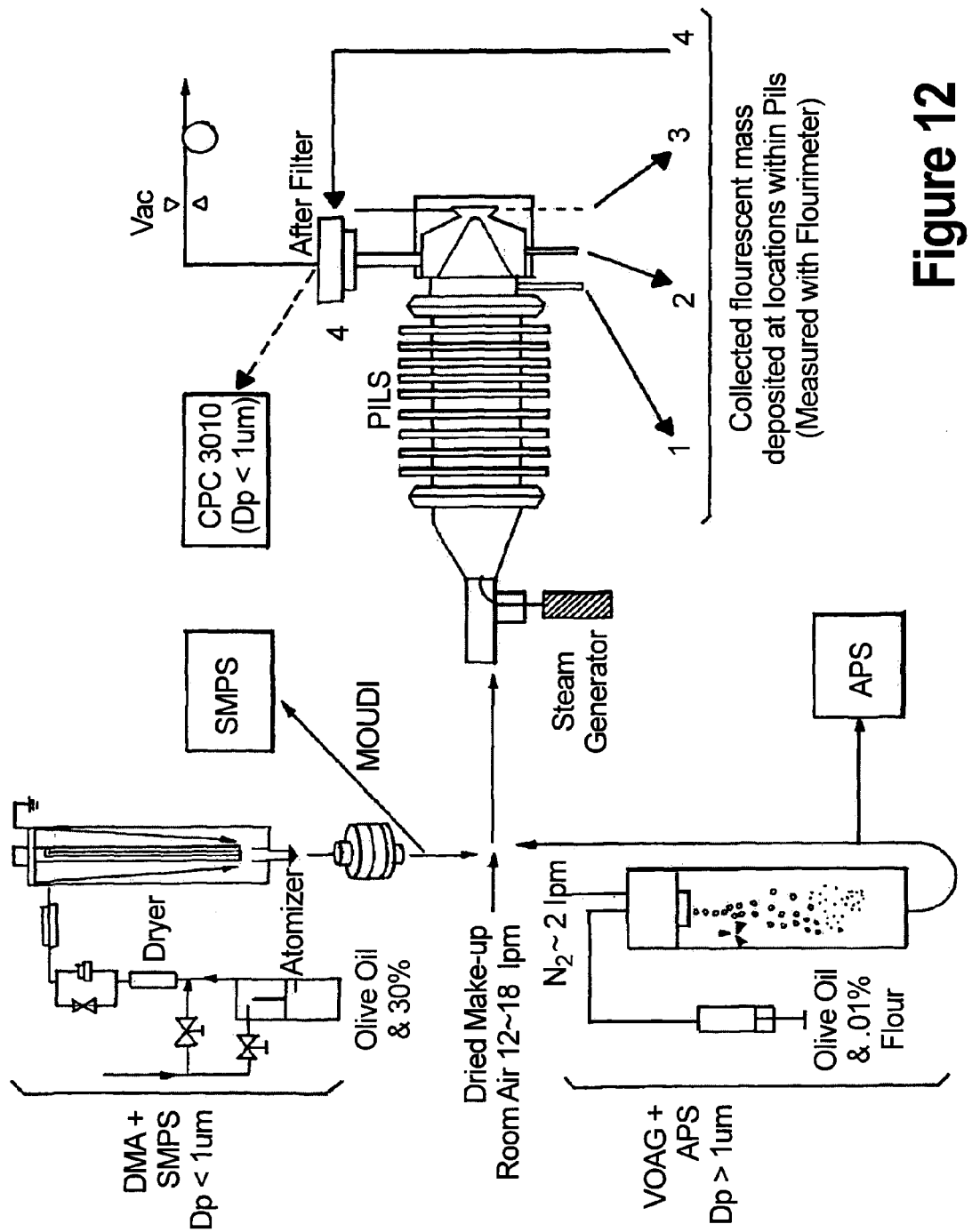
FIG. 12 is a schematic diagram illustrating two methods of particle generation utilized to calibrate the size-dependent efficiency of PILS II.

In order to calibrate the size-dependant collection efficiency of PILS II, two standard methods of particle generation were needed to cover the large particle size range as shown in FIG. 12. For particle diameters Dp>1 µm, a vibrating orifice aerosol generator (VOAG) (VOAG 3450, TSI Inc, St Paul Minn.) produced aerosols out of a solution of olive oil (0.1–10%) and propanol, tagged with a small amount of flouresceine (0.01%, Aldrich Chemical). The size of the aerosols generated depended on the fraction of olive oil in solution and the VOAG operating frequency. The VOAG illustrated in FIG. 12 was turned upside-down to maximize transport of large particles in about 2 l min$^{-1}$ of nitrogen dilution air. An aerodynamic particle sizer (APS) located just before the PILS, monitored the diameter of the generated aerosol. To accommodate the total flow of PILS II and APS, 18 l min$^{-1}$ of dried ambient room air was added. The purpose of the dried make-up air was to mimic more closely field operation by embedding the calibration aerosol in a dry ambient aerosol while testing the collection efficiency at low relative humidity. No sensitivity to relative humidity (RH) was found for RHs as low as from about 10 to about 13%.

For particles Dp<1 µm, an atomizer in series with a Differential Mobility Analyzer (DMA) generated a polydisperse aerosol also from a solution containing flouresceine. Following the DMA an inline impactor removed doublets and larger particles before being scanned with a Scanning Mobility Particle Spectrometer (SMPS). The relative particle loss inside PILS II was determined by washing out the fluorescent mass from the separate components and quantifying with a flourimeter (Shimadzu RF-Mini 150). An after-filter placed downstream of PILS II collected any particle mass that penetrated the entire instrument. This filter was extracted by sonication in water after each run. A condensation particle counter (CPC) (CPC 3010, TSI Inc.) was also added downstream of PILS II to measure concentrations of sub-micron particles. Because of their small mass, particles of these sizes were difficult to extract accurately with the filter due to high background concentration relative to filter loading. The four separate regions of collected flouresceine and the possible reasons for deposition are as illustrated in FIG. 12:
 1. Body of PILS: Deposition due to turbulent loss and gravitational settling of droplets.
 2. Impactor Loss: Droplet deposition inside the inner nozzle plus impacted droplets not collected in the impaction cavity.

3. Collected Sample: Mass collected in continuous flow for analysis.

4. Penetrated mass: All mass not removed by PILS II.

Figure 13:
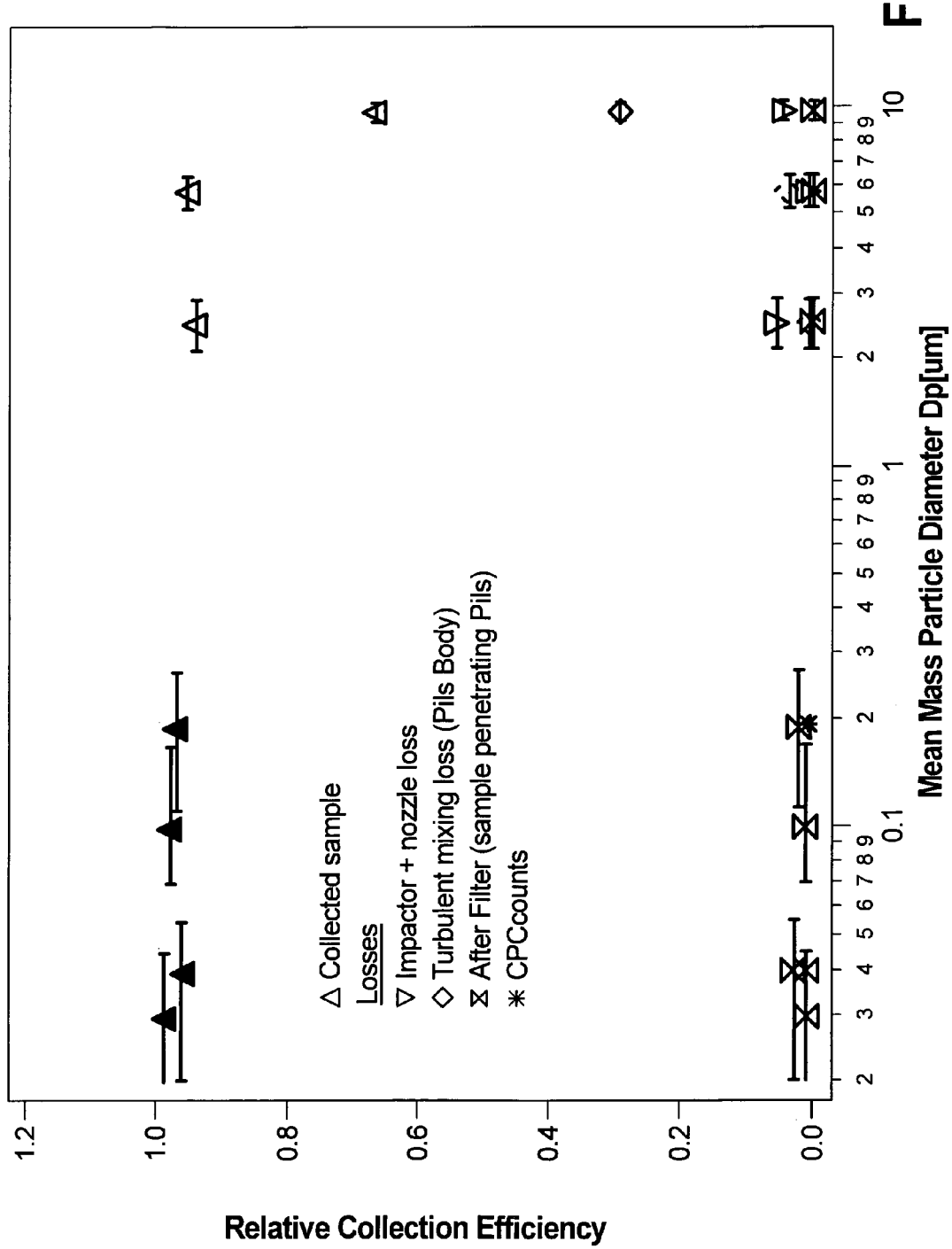
FIG. 13 is a graph showing efficiency curves for particles generated as shown in FIG. 12.

FIG. 13 shows the efficiency curves for both size ranges at about 13% relative humidity. For larger particles, the collection efficiency begins to drop off at Dp of about 10 μm, where particle loss in the mixing and growth regions of the PILS II increases. For particles having Dp<1 μm there is no appreciable loss down to about 30 nm. The gap in the graph near Dp~1 μm, results from the size limits of the two aerosol generation techniques.

In PILS II, the present steam generator produces a steady, high velocity turbulent jet of water vapor (Reynolds number of about 4000) to achieve rapid near-adiabatic mixing with the aerosol sample to maximize the super-saturation of aerosol particles. When PILS II was operated with a total filter on the sample inlet, a broad droplet distribution, similar to FIG. 5, yet smaller, was observed. This indicated that supersaturation was sufficient to achieve homogeneous nucleation of the water vapor, and that activation of small particles was not an issue.

Experiments with a fluorescent calibration aerosols made possible the direct visual observation of particle collection and loss within the PILS II. This enabled the testing of design changes on-the-spot and aided greatly in our understanding of the flow dynamics. The conical expansion in the wall of PILS II at the point of steam injection and mixing reduces droplet transport to the wall. In addition, the aerosol sample enters parallel to the flow of steam, eliminating the 90° turn. With these changes, PILS II was able to collect particles of larger size than PILS I. For example the size of the particles increased to nearly 10 μm, at which point deposition in the body started to increase due to turbulence and gravitational settling.

Calibration aerosols generated from solutions of olive oil and flouresceine described above showed that PILS II could collect 97% of the particle mass in a 15 l min$^{-1}$ sample flow, the particle ranging in size from about 30 nm to about 10 μm. The output of PILS II was an adjustable liquid water flow (0.05–0.5 ml min$^{-1}$) containing the soluble aerosol species to be measured. In PILS II-IC system, a Metrohm 761 IC coupled to PILS II allowed for online speciation of anion and cation species with respective LODs of 10 ng m$^{-3}$ and 50 ng m$^{-3}$. With the appropriate columns and eluants, the speciation of the major aerosol inorganics was possible within 4 minutes, with extended times of 15 to 30 minutes required for soluble organic acids.

The present invention may be better understood by reference to the following non-limiting Examples, which are provided as exemplary of the invention. The following Examples are presented in order to more fully illustrate the preferred embodiments of the invention. They should in no way be construed, however, as limiting the broad scope of the invention.

REFERENCES

The following publications as mentioned in the foregoing specification, are incorporated herein by reference as if set forth in full for all they disclose:

Boring, C. B., R. Al-Horr, Z. Genfa, and P. K. Dasgupta, "Field Measurement of acidic gases and soluble anions in atmospheric particulate matter using a parallel plate wet denuder and an alternating fiber-based automated analysis system," Anal. Chem., 74, 1256–1268, (2002).

Buhr, S. M., M. P. Buhr, F. C. Fehsenfeld, J. S. Holloway, U. Karst, R. B. Norton, D. D. Parrish, and R. E. Sievers, "Development of a semi-continuous method for the measurement of nitric acid vapor and particulate nitrate and sulfate," Atmos. Environ. 29: 2609–2624, (1995).

Carson, P. G., K. R. Neubauer, M. V. Johnston, and A. S. Wexler, "On-line chemical analysis of aerosols by rapid single-particle mass spectrometry," J. Aerosol Sci. 26: 535–545, (1995).

Chow, J. C., "Measurement methods to determine compliance with ambient air quality standards for suspended particles," J. Air Wast Mang. 45: 320–382, (1995).

Hinz, K. P., R. Kaufmann, and B. Spengler, "Laser-induced mass analysis of single particles in the airborne state," Analyt. Chem. 66: 2017–2076, (1994).

Ito, K., C. C. Chasteen, H. Chung, S. K. Prouthoor, Z. Genfa, and P. K. Dasgupta, "A continuous monitoring system for strong acidity in aerosols," Anal. Chem. 70: 2839–2847, (1998).

Jayne, J. T., D. C. Leard, X. Zhang, P. Davidovits, K. A. Smith, C. E. Kolb, and D. R. Worsnop, "Aerosol mass spectrometer for size and composition analysis of submicron particles," J. Aerosol Sci., submitted, (1998).

Karlsson, A., K. Irgum, and H. Hansson, "Single-stage flowing liquid film impactor for continuous on-line particle analysis," J. Aerosol Sci. 28: 1539–1551, (1997).

Khlystov, A., G. P. Wyers, and J. Slanina, "The steam-jet aerosol collector," Atmos. Envir. 29: 2229–2234, (1995).

Knutson, E. O., and K. T. Whitby, "Aerosol classification by electrical mobility: Apparatus, theory, and applications," J. Aerosol Sci. 6: 443–451, (1975).

Kogan, Y. I., and Z. A. Burnasheva, "Growth and measurement of condensation nuclei in a continuous stream," Russian J. Phys. Chem. 34: 1240–1243, (1960).

Kousaka, Y., T. Niida, K. Okuyama, and H. Tanaka, "Development of a mixing type condensation nucleus counter," J. Aerosol Sci. 13: 231–240, (1982).

Liu, S., and P. K. Dasgupta, "Automated system for chemical analysis of airborne particles based on corona-free electrostatic collection," Anal. Chem. 68: 3638–3644, (1996).

Marijinissen, J. C. M., B. Scarlett, and P. J. T. Verheijen, "Proposed on-line aerosol analysis combining size determination, laser-induced fragmentation and time-of-flight mass spectroscopy," J. Aerosol Sci. 19: 1307, (1988).

Marple, V. A., and K. Willeke, "Impactor design," Atmos. Env., 10, 891–896, (1976).

McKeown, P. J., M. V. Johnston, and D. D. Murphy, "On-line single-particle aerosol analysis by laser desorption mass spectrometry," Analyt. Chem. 63: 2069, (1991).

Okuyama, K., Y. Kousaka, and T. Motouchi, "Condensational growth of ultrafine aerosol particles in a new particle size magnifier," Aerosol Sci. and Technol. 3: 353–366, (1984).

Oms, M. T., P. A. C. Jongejan, A. C. Veltkamp, G. P. Wyers, and J. Slanina, "Continuous monitoring of atmospheric HCL, HNO3, HNO2, and SO2 by wet-annular denuder sampling with on-line chromatographic analysis," Intern. J. Anal. Chem. 2: 207–218, (1997).

Poruthoor, S. K., and P. K. Dasgupta, "Automated particle collection and analysis. Near-real time measurement of aerosol cerium (III)," Analytica Chemica Acta 361: 151–159, (1998).

Prather, K. A., T. Nordmeyer, and K. Salt, "Real-time characterization of individual aerosol particles using time-of-flight mass spectrometry," Analyt. Chem. 66: 1403, (1994).

Rader, D. J., and V. A. Marple, "Effect of ultra-stokesian drag and particle interception on impaction characteristics," Aerosol Sci. Technol. 4: 141–156, (1985).

Reents, W. D. J., A. M. Mujsce, A. J. Muller, D. J. Siconolfi, and A. G. Swanson, "Real-time elemental analysis of individual submicron particles by laser ablation time-of-flight mass spectrometry," J. Aerosol Sci. 23: 263, (1995).

Simon, P. K., and P. K. Dasgupta, "Continuous automated measurement of the soluble fraction of atmospheric particulate matter," Anal. Chem. 67: 71–78, (1995).

Slanina, J., H. M. T. Brink, R. P. Otjes, A. Even, P. Jongejan, A. Khlystov, A. Waijers-Ijpelaan, M. Hu, and Y. Lu, "The continuous analysis of nitrate and ammonium in aerosols by the steam jet aerosol collector (SJAC): Extension and validation of the methodology," "Atmos. Envir., 35, 2319–2330, (2001).

Stolzenburg, M. R., and V. Hering, "A method for the automated measurement of fine particle nitrate in the atmosphere," Environ. Sci. Technol, submitted, (1999).

Turpin, B. J., R. A. Cary, and J. J. Huntzicker, "An in situ, time-resolved analyzer for aerosol organic and elemental carbon," J. Aerosol Sci. 12: 161–171, (1990).

Wang, S. C., and R. C. Flagan, "Scanning electrical mobility spectrometer," Aerosol Sci. Technol. 13: 230–240, (1990).

Zellweger, C., M. Ammann, P. Hofer, and U. Baltensperger, "NOy speciation with a combined wet effluent diffusion denuder-aerosol collector coupled to ion chromatography," Atm. Envir. 33: 1131–1140, (1999).

Thus, while there have been described what are presently believed to be the preferred embodiments of the present invention, those skilled in the art will realize that other and further modifications can be made to the invention without departing from the true spirit of the invention, such further and other modifications are intended to be included herein within the scope of the appended claims.

We claim:

1. An enhanced apparatus for continuous on-line measurement of chemical composition of aerosol particles which comprises:
   an enhanced particle size magnifier including:
   a mixing chamber having a first inlet, a second inlet and an outlet, said first inlet adapted to receive sample air carrying aerosol particles said second inlet adapted to receive steam, said steam inlet positioned at about a 90° angle with said sample air inlet, said steam inlet having a steam outlet positioned such that the steam and the sample air flow in the same direction;
   a growth chamber for growth and activation of said aerosol particles, said growth chamber having walls and being disposed downstream of and in fluid communication with said mixing chamber;
   a collection device for said activated aerosol particles disposed downstream of and in fluid communication with said growth chamber, said collection device having a nozzle means and a housing encapsulating said nozzle means, said housing having an impaction surface opposite said nozzle means, means for drawing sample air in communication with said housing, means adapted to receive carrier water and drain means; and
   analytical means for measuring chemical composition of said activated aerosol particles disposed downstream and in fluid communication with said collection device;
   said means for drawing sample air connected to a vacuum source for directing said sample air carrying said activated aerosol particles through said nozzle means to form a jet stream;
   said jet stream impinging said activated aerosol particles upon said impaction surface;
   said impaction surface having a groove along its perimeter, said groove adapted to receive wicking fibers;
   said means adapted to receive carrier water for flushing said impinged activated aerosol particles from said impaction surface into a liquid stream for transport to said analytical means.

2. The apparatus of claim 1, wherein said growth chamber is capable of maintaining said walls at about room temperature in the absence of means for cooling.

3. The apparatus of claim 1, wherein said sample air carrying aerosol particles is drawn into said mixing chamber from about 20 L min$^{-1}$ to about 10 L min$^{-1}$.

4. The apparatus of claim 1, wherein said aerosol particles that are activated have a diameter from about 30 nm to about 20 micrometers.

5. The apparatus of claim 1, wherein said growth chamber is a condenser for removal of excess water vapor.

6. The apparatus of claim 7, wherein said condenser has a length from about 10 cm to about 20 cm.

7. The apparatus of claim 1, further comprising means for cooling said condenser.

8. The apparatus of claim 7, wherein said means for cooling said condenser is at least one fin.

9. The apparatus of claim 1, wherein said collection device is a nozzle impactor having a single orifice and said impaction surface is a substantially flat vertical disc.

10. The apparatus of claim 1, wherein said groove is ring shaped.

11. The apparatus of claim 10, wherein said wicking fibers are adapted to collect liquid from impacted activated aerosol particles.

12. The apparatus of claim 1, wherein said analysis is provided by analytical means selected from the groups consisting of ion chromatography, capillary electrophoresis, gas chromatography, high pressure liquid chromatography, total organic carbon analyzer, liquid particle counters, and liquid chromatography/mass spectrometry.

13. The apparatus of claim 1, further comprising a steam saturator in fluid communication with said mixing chamber for providing steam to said second inlet, said saturator comprising a first stainless steal tubing adapted to receive a steady flow of purified water and a temperature controlled cartridge heater, said first tubing coiled around said cartridge heater, said first tubing adapted to receive a second tubing in fluid communication with said second inlet, said second tubing being bent such that the steam and the sample air flow in the same direction along the centerline of said apparatus.

* * * * *